(12) United States Patent
Lee et al.

(10) Patent No.: US 7,977,341 B2
(45) Date of Patent: Jul. 12, 2011

(54) SUBSTITUTED ISOXAZOLES AS FUNGICIDES

(75) Inventors: Shy-Fuh Lee, Sunnyvale, CA (US); Micah Gliedt, San Jose, CA (US)

(73) Assignee: Syngenta Limited, Surrey (GB)

( * ) Notice: Subject to any disclaimer, the term of this patent is extended or adjusted under 35 U.S.C. 154(b) by 934 days.

(21) Appl. No.: 11/574,892

(22) PCT Filed: Sep. 9, 2005

(86) PCT No.: PCT/US2005/032080
§ 371 (c)(1), (2), (4) Date: Aug. 20, 2007

(87) PCT Pub. No.: WO2006/031631
PCT Pub. Date: Mar. 23, 2006

(65) Prior Publication Data
US 2008/0096843 A1     Apr. 24, 2008

Related U.S. Application Data

(60) Provisional application No. 60/608,589, filed on Sep. 10, 2004, provisional application No. 60/616,017, filed on Oct. 5, 2004.

(51) Int. Cl.
*C07D 413/06* (2006.01)
*A01N 43/80* (2006.01)

(52) U.S. Cl. ...... 514/256; 514/340; 544/333; 546/272.1

(58) Field of Classification Search ................. 544/333; 546/272.1; 514/256, 340
See application file for complete search history.

(56) References Cited

U.S. PATENT DOCUMENTS
5,064,847 A    11/1991  Hubl et al.

FOREIGN PATENT DOCUMENTS
WO         WO 95/01979        *   1/1995

OTHER PUBLICATIONS
Della Croce et al., CAPLUS Abstract 133:17441 (2000).*
Kurihara et al., CAPLUS Abstract 113:59122 (1990).*

* cited by examiner

*Primary Examiner* — Deepak Rao
(74) *Attorney, Agent, or Firm* — Rebecca A. Howard

(57) ABSTRACT

The present invention provides compounds of formula I: (I) along with methods of making the same, compositions thereof, and methods of use thereof, particularly methods of use as fungicides.

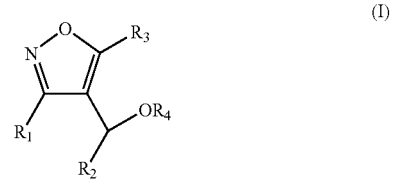

33 Claims, No Drawings

SUBSTITUTED ISOXAZOLES AS FUNGICIDES

RELATED APPLICATIONS

This application is a 371 of International Application No. PCT/US2005/032080 filed Sep. 9, 2005, which claims priority to U.S. Ser. No. 60/608,589 filed Sep. 10, 2004, and U.S. Ser. No. 60/616,017 filed Oct. 5, 2004, the contents of which are incorporated herein by reference.

FIELD OF THE INVENTION

The present invention concerns substituted isoxazoles, compositions thereof, and methods of use thereof for the control of microbial pests, particularly fungal pests, on plants.

BACKGROUND OF THE INVENTION

The incidence of serious fungal infections, either systemic or topical, continues to increase for plants, animals, and humans. Many fungi are common in the environment and not harmful to plants or mammals. However, some fungi can produce disease in plants, humans and/or animals.

Fungicides are compounds, of natural or synthetic origin, which act to protect plants against damage caused by fungi, including oomycetes. Current methods of agriculture rely heavily on the use of fungicides. In fact, some crops cannot be grown usefully without the use of fungicides. Using fungicides allows a grower to increase the yield of the crop and consequently, increase the value of the crop. Numerous fungicidal agents have been developed. However, the treatment of fungal infestations and infections continues to be a major problem. Furthermore, fungicide and antifungal drug resistance has become a serious problem, rendering these agents ineffective for some agricultural and therapeutic uses. As such, a need exists for the development of new fungicidal and antifungal compounds (see, e.g., U.S. Pat. No. 6,673,827; See also U.S. Pat. No. 6,617,330 to Walter, which describes pyrimidin-4-enamine as fungicides).

U.S. Pat. No. 5,627,137 to R. Anderson et al. describes the preparation of azinylphthalides and related compounds as herbicides.

U.S. Pat. No. 5,679,692 to R. Friary et al. describes the preparation of pyridylcarbonylpiperidine-4-methanols and analogs as antihistaminics and platelet activating factor antagonists.

SUMMARY OF THE INVENTION

A first aspect of the present invention is a compound of formula I:

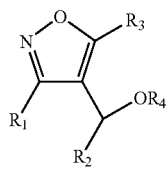

wherein:

$R_1$ is alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, or nitro; or heteroaryl optionally substituted with halogen, alkyl, alkenyl, alkynyl, haloalkyl, alkoxy, alkylthio, haloalkoxy, cyano, or nitro;

$R_2$ is alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, or nitro; heteroaryl, especially 2-, 3- or 4-pyridyl optionally substituted with halogen, alkyl, alkenyl, alkynyl, haloalkyl, alkoxy, alkylthio, haloalkoxy, cyano, or nitro; 5-pyrimidinyl optionally substituted with halogen, alkyl, alkenyl, alkynyl, haloalkyl, alkoxy, alkylthio, haloalkoxy, cyano, or nitro; or 2- or 5-thiazolyl optionally substituted with halogen, alkyl, alkenyl, alkynyl, alkoxy, alkylthio, haloalkyl, cyano, or nitro, $R_3$ is H; alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryloxyalkyl optionally substituted with halogen, alkyl, alkenyl, alkynyl, haloalkyl, alkoxy, alkylthio, haloalkoxy, cyano, or nitro; arylthioalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, or nitro; or alkylsilyl.

$R_4$ is H; acyl (e.g., acetyl, benzoyl, phenylacetyl); haloacyl; alkoxycarbonyl; aryloxycarbonyl; alkylaminocarbonyl; or dialkylaminocarbonyl;

or a salt thereof.

The compounds and compositions of the present invention are useful as crop protection agents to combat or prevent fungal infestations, or to control other pests such as weeds, insects, or acarids that are harmful to crops.

A second aspect of the present invention is a composition for controlling and preventing plant pathogenic microorganisms comprising, in combination, an active compound or combination of compounds as described herein together with a suitable carrier.

A third aspect of the present invention is a method of controlling or preventing infestation of cultivated plants by pathogenic microorganisms, comprising applying an active compound or combination of compounds as described herein to said plants, parts thereof or the locus thereof in an amount effective to control said microorganisms.

A further aspect of the present invention is a method of controlling or preventing infestation of technical materials by pathogenic microorganisms, comprising applying an active compound as described herein to said technical materials, parts thereof or the locus thereof in an amount effective to control said microorganisms.

A further aspect of the present invention is a method of treating a fungal infection in a subject in need thereof, comprising administering an active compound as described herein to said subject in an amount effective to treat said fungal infection.

A still further aspect of the present invention is the use of an active compound as described herein for the preparation of a composition (e.g., an agricultural formulation, a pharmaceutical formulation) for carrying out a method as described herein (e.g., an agricultural treatment as described herein, the treatment of technical materials as described herein, the treatment of a fungal infection in a subject as described herein).

The foregoing and other objects and aspects of the present invention are explained in greater detail below.

DETAILED DESCRIPTION OF THE PREFERRED EMBODIMENTS

"Alkyl" as used herein refers to a saturated hydrocarbon radical which may be straight-chain or branched-chain (for example, ethyl, isopropyl, t-amyl, or 2,5-dimethylhexyl) or cyclic (for example cyclobutyl, cyclopropyl or cyclopentyl) and contains from 1 to 24 carbon atoms. This definition applies both when the term is used alone and when it is used as part of a compound term, such as "haloalkyl" and similar terms. In some embodiments, preferred alkyl groups are those containing 1 to 4 carbon atoms, which are also referred to as "lower alkyl." In some embodiments preferred alkyl groups are those containing 5 or 6 to 24 carbon atoms, which may also be referred to as "higher alkyl".

"Alkenyl," as used herein, refers to a straight or branched chain hydrocarbon containing from 2 to 24 carbons and containing at least one carbon-carbon double bond formed by the removal of two hydrogens. Representative examples of "alkenyl" include, but are not limited to, ethenyl, 2-propenyl, 2-methyl-2-propenyl, 3-butenyl, 4-pentenyl, 5-hexenyl, 2-heptenyl, 2-methyl-1-heptenyl, 3-decenyl and the like. "Lower alkenyl" as used herein, is a subset of alkenyl and refers to a straight or branched chain hydrocarbon group containing from 1 to 4 carbon atoms.

"Alkynyl," as used herein, refers to a straight or branched chain hydrocarbon group containing from 2 to 24 carbon atoms and containing at least one carbon-carbon triple bond. Representative examples of alkynyl include, but are not limited, to acetylenyl, 1-propynyl, 2-propynyl, 3-butynyl, 2-pentynyl, 1-butynyl and the like. "Lower alkynyl" as used herein, is a subset of alkyl and refers to a straight or branched chain hydrocarbon group containing from 1 to 4 carbon atoms.

"Alkoxy" refers to an alkyl radical as described above which also bears an oxygen substituent which is capable of covalent attachment to another hydrocarbon radical (such as, for example, methoxy, ethoxy and t-butoxy).

"Alkylthio" as used herein refers to an alkyl group, as defined herein, appended to the parent molecular moiety through a thio moiety, as defined herein. Representative examples of alkylthio include, but are not limited to, methylthio, ethylthio, tert-butylthio, hexylthio, and the like.

"Aryl" or "aromatic ring moiety" refers to an aromatic substituent which may be a single ring or multiple rings which are fused together, linked covalently or linked to a common group such as an ethylene or methylene moiety. The aromatic rings may each contain heteroatoms and hence "aryl" encompasses "heteroaryl" as used herein. Representative examples of aryl include, azulenyl, indanyl, indenyl, naphthyl, phenyl, tetrahydronaphthyl, biphenyl, diphenylmethyl, 2,2-diphenyl-1-ethyl, thienyl, pyridyl and quinoxalyl. "Aryl" means substituted or unsubstituted aryl unless otherwise indicated and hence the aryl moieties may be optionally substituted with halogen atoms, or other groups such as nitro, carboxyl, alkoxy, phenoxy and the like. Additionally, the aryl radicals may be attached to other moieties at any position on the aryl radical which would otherwise be occupied by a hydrogen atom (such as, for example, 2-pyridyl, 3-pyridyl and 4-pyridyl).

"Heteroaryl" means a cyclic, aromatic hydrocarbon in which one or more carbon atoms have been replaced with heteroatoms. If the heteroaryl group contains more than one heteroatom, the heteroatoms may be the same or different. Examples of heteroaryl groups include pyridyl, pyrimidinyl, imidazolyl, thienyl, furyl, pyrazinyl, pyrrolyl, pyranyl, isobenzofuranyl, chromenyl, xanthenyl, indolyl, isoindolyl, indolizinyl, triazolyl, pyridazinyl, indazolyl, purinyl, quinolizinyl, isoquinolyl, quinolyl, phthalazinyl, naphthyridinyl, quinoxalinyl, isothiazolyl, and benzo[b]thienyl. Preferred heteroaryl groups are five and six membered rings and contain from one to three heteroatoms independently selected from O, N, and S. The heteroaryl group, including each heteroatom, can be unsubstituted or substituted with from 1 to 4 substituents, as chemically feasible. For example, the heteroatom S may be substituted with one or two oxo groups, which may be shown as =O.

"Agriculturally acceptable salt" means a salt the cation of which is known and accepted in the art for the formation of salts for agricultural or horticultural use. Preferably the salts are water-soluble.

"Cyano" as used herein refers to a —CN group.

"Halo" or "halogen," as used herein, refers to —Cl, —Br, —I or —F.

"Haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, 2-chloro-3-fluoropentyl, and the like.

"Hydroxy," as used herein, refers to an —OH group.

"Nitro," as used herein, refers to a —$NO_2$ group.

"Oxy," as used herein, refers to a —O— moiety.

"Thio," as used herein, refers to a —S— moiety.

"Organic base" as used herein includes but is not limited to triethylamine, triisobutylamine, triiooctylamine, triisodecylamine, diethanolamine, triethanolamine, pyridine, morpholine, and mixtures thereof. A preferred category of organic bases is organic amines.

"Inorganic base" as used herein includes but is not limited to sodium carbonate, sodium bicarbonate, potassium carbonate, and mixtures thereof.

"Inert solvent" as used herein includes any suitable inert solvent, such as tetrahydrofuran, N-methylpyrrolidone, dimethylformamide, toluene, dimethyl ether, methyl t-butyl ether and dioxane, methylene chloride, chloroform, 1,2-dichloroethane, and mixtures thereof.

"Protic solvent" as used herein may be any suitable protic solvent, including but not limited to methanol, ethanol, isopropanol, n-butanol, ethylene glycol, methyl Cellosolve, ethyl Cellosolve, cyclohexanol, glycerol, diethylene glycol, triethanolamine, polyethylene glycol, sec-butanol, n-propanol and tert-butanol.

The disclosures of all US Patent references cited herein are to be incorporated herein in their entirety as if fully set forth.

2. Compounds. The compounds of this invention are represented by the structure I:

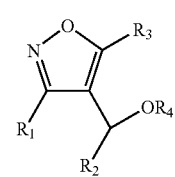

wherein:

$R_1$ is alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, or nitro; or heteroaryl optionally substituted with halogen, alkyl, alkenyl, alkynyl, haloalkyl, alkoxy, alkylthio, haloalkoxy, cyano, or nitro;

$R_2$ is alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, or nitro; heteroaryl, especially 2-, 3- or 4-pyridyl optionally substituted with halogen, alkyl, alkenyl, alkynyl, haloalkyl, alkoxy, alkylthio, haloalkoxy, cyano, or nitro; 5-pyrimidinyl optionally substituted with halogen, alkyl, alkenyl, alkynyl, haloalkyl, alkoxy, alkylthio, haloalkoxy, cyano, or nitro; or 2- or 5-thiazolyl optionally substituted with halogen, alkyl, alkenyl, alkynyl, alkoxy, alkylthio, haloalkyl, cyano, or nitro, $R_3$ is H; alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryloxyalkyl optionally substituted with halogen, alkyl, alkenyl, alkynyl, haloalkyl, alkoxy, alkylthio, haloalkoxy, cyano, or nitro; arylthioalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, or nitro; or alkylsilyl.

$R_4$ is H; acyl (e.g., acetyl, benzoyl, phenylacetyl); haloacyl; alkoxycarbonyl; aryloxycarbonyl; alkylaminocarbonyl; or dialkylaminocarbonyl.

Methods of making. Compositions of generic structure I wherein $R_4$=H may be prepared by the [3+2]-cycloaddition of a carboximidoyl chloride II with acetylenic carbinol III:

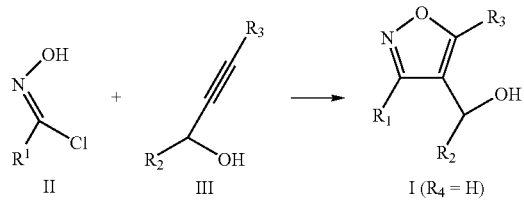

The reaction is carried out in the presence of an organic base such as triethylamine in an inert solvent such as DCE (1,2-dichloroethane), or an inorganic base such as sodium bicarbonate in a protic solvent such as isopropanol. Time and temperature of the reaction is not critical but may be at temperatures ranging from 20-60° C. for 1-24 hr.

The carboximidoyl chlorides II are prepared from the corresponding oximes using chlorinating reagents such as N-chlorosuccinimide or sodium hypochlorite (bleach), or are obtained from commercial sources.

The acetylenic carbinols III are obtained by addition of an organometallic acetylene IV (M=Li, MgX; X=Cl, Br) to an aldehyde $R_2$CHO (V), as shown below:

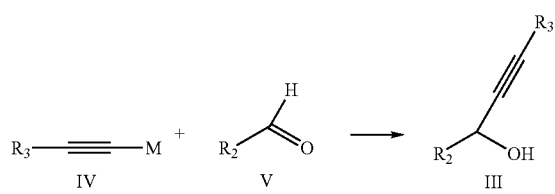

In certain cases, the [3+2]-cycloaddition proceeds more rapidly and in higher yield when the corresponding ketone (VI) of acetylenic carbinol III is used:

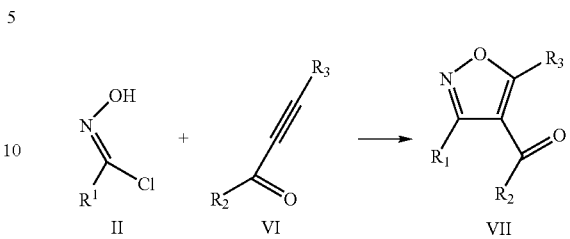

Compounds of Formula VII are useful for making compounds of Formula I as described below, where the isoxazole VII is reduced (e.g., with sodium borohydride) to give I.

In some cases, the regioisomer of I is produced along with I in the [3+2]-cycloaddition. This regioisomer VIII generally is less active than 1 in bioevaluation.

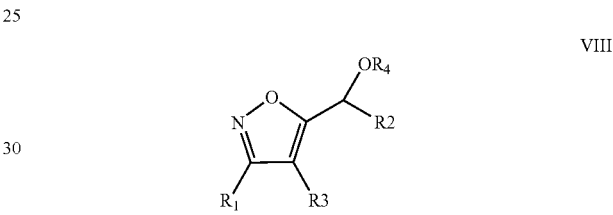

Acetylenic ketone VI can be prepared from III by oxidation, for example with IBX (o-iodosobenzoic acid) in an inert solvent such as DMSO (dimethylsulfoxide) at any suitable time and temperature (e.g., 20° C. for 1-2 hr). Reduction of isoxazole VII with sodium borohydride in alcoholic solvent (e.g., ethanol) at 0° C. for 0.3-2 hr produces the isoxazole I ($R_4$=H).

Isoxazoles in which $R_4 \neq H$ are prepared from I ($R_4$=H) using standard acylation or carbamoylation conditions. For example, the acetate derivative of I ($R_4$=COCH$_3$) is synthesized from the alcohol I (R=H) by reaction with acetic anhydride and pyridine in ether solvent at room temperature overnight. Acylations may be carried out using either acid anhydrides (e.g., acetic anhydride, propionic anhydride) or acid chlorides (e.g., benzoyl chloride) in the presence of an organic base in an inert solvent (e.g., ether, dichloromethane). Carbamoylations are effected by treating alcohols I with a strong base such as sodium hydride followed by a carbamoyl chloride (e.g., N,N-dimethylcarbamoyl chloride) in an inert solvent such as DMF (dimethylformamide).

Exemplary compounds. Compounds of the invention that are especially useful for the control of fungal pathogens are those in which:

$R_1$=alkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, nitro; or heteroaryl optionally substituted with halogen, alkyl, alkenyl, alkynyl, haloalkyl, alkoxy, alkylthio, haloalkoxy, cyano, nitro, $R_2$=heteroaryl, especially 2-, 3- or 4-pyridyl optionally substituted with halogen, alkyl, alkenyl, alkynyl, haloalkyl, alkoxy, alkylthio, haloalkoxy, cyano, nitro; or 5-pyrimidinyl optionally substituted with halogen, alkyl, alkenyl, alkynyl, haloalkyl, alkoxy, alkylthio, haloalkoxy, cyano, or nitro;

$R_3$=alkyl; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, nitro; or alkylsilyl; and $R_4$=H.

Examples of compounds of the present invention include, but are not limited to, the following:

| Compound No. | Structure | Chemical Name |
|---|---|---|
| 1 | 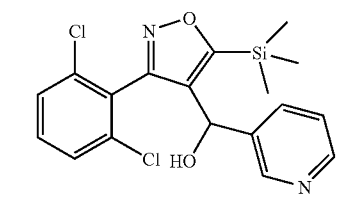 | 3-(2,6-Dichlorophenyl)-4-[(3-pyridyl)hydroxymethyl]-5-trimethylsilylisoxazole |
| 2 | 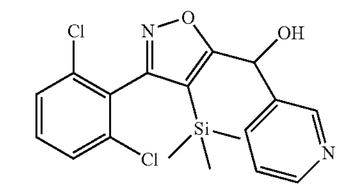 | 3-(2,6-Dichlorophenyl)-5-[(3-pyridyl)hydroxymethyl]-4-trimethylsilylisoxazole |
| 3 | 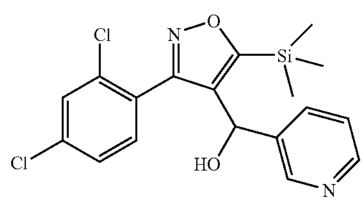 | 3-(2,4-Dichlorophenyl)-4-[(3-pyridyl)hydroxymethyl]-5-trimethylsilylisoxazole |
| 4 | 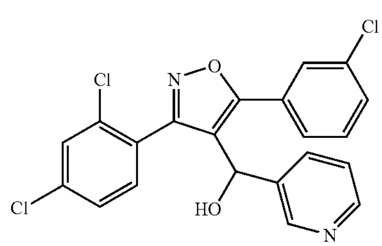 | 5-(3-Chlorophenyl)-3-(2,4-dichlorophenyl)-4-[(3-pyridyl)hydroxymethyl]-isoxazole |
| 5 | 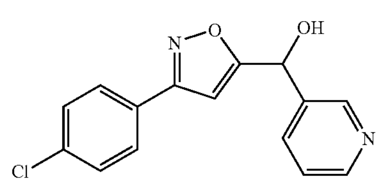 | 3-(4-Chlorophenyl)-5-[(3-pyridyl)hydroxymethyl]-isoxazole |
| 6 | 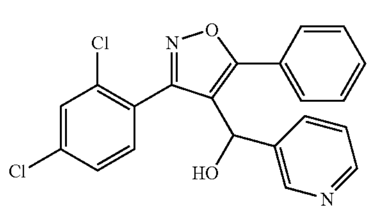 | 3-(2,4-Dichlorophenyl)-4-[(3-pyridyl)hydroxymethyl]-5-phenylisoxazole |

-continued

| Compound No. | Structure | Chemical Name |
|---|---|---|
| 7 | 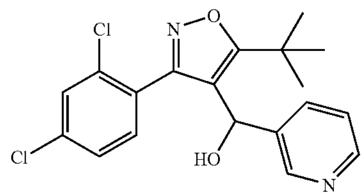 | 3-(2,4-Dichlorophenyl)-5-(1,1-dimethylethyl)-4-[(3-pyridyl)hydroxymethyl]-isoxazole |
| 8 | 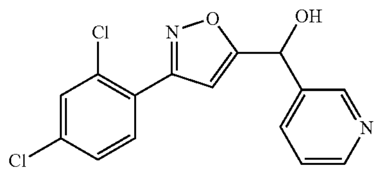 | 3-(2,4-Dichlorophenyl)-5-[(3-pyridyl)hydroxymethyl]-isoxazole |
| 9 | 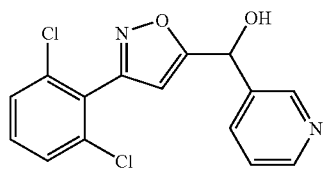 | 3-(2,6-Dichlorophenyl)-5-[(3-pyridyl)hydroxymethyl]-isoxazole |
| 10 | 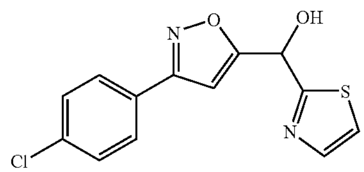 | 3-(4-Chlorophenyl)-5-[(2-thiazolyl)hydroxymethyl]-isoxazole |
| 11 | 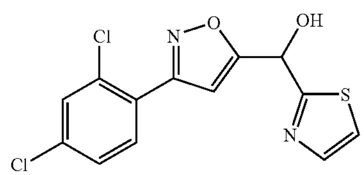 | 3-(2,4-Dichlorophenyl)-5-[(2-thiazolyl)hydroxymethyl]-isoxazole |
| 12 | 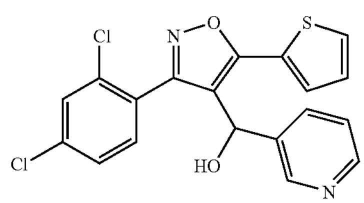 | 3-(2,4-Dichlorophenyl)-4-[(3-pyridyl)hydroxymethyl]-5-(2-thienyl)isoxazole |
| 13 | 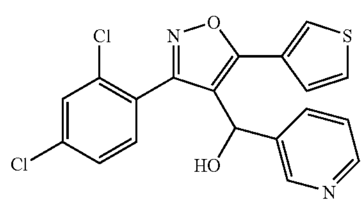 | 3-(2,4-Dichlorophenyl)-4-[(3-pyridyl)hydroxymethyl]-5-(3-thienyl)isoxazole |
| 14 | 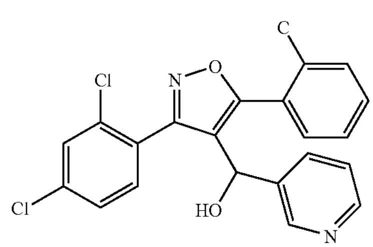 | 5-(2-Chlorophenyl)-3-(2,4-dichlorophenyl)-4-[(3-pyridyl)hydroxymethyl]-isoxazole |

-continued

| Compound No. | Structure | Chemical Name |
|---|---|---|
| 15 | 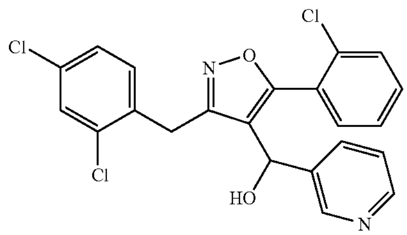 | 5-(2-Chlorophenyl)-3-(2,4-dichlorobenzyl)-4-[(3-pyridyl)hydroxymethyl]-isoxazole |
| 16 | 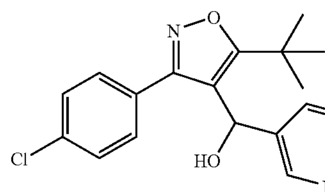 | 3-(4-Chlorophenyl)-5-(1,1-dimethylethyl)-4-[(3-pyridyl)hydroxymethyl]-isoxazole |
| 17 | 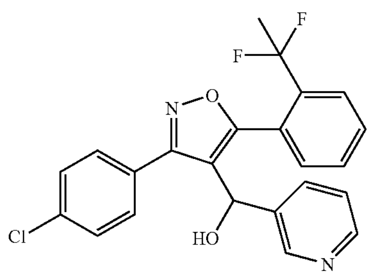 | 3-(4-Chlorophenyl)-4-[(3-pyridyl)hydroxymethyl]-5-(2-trifluoromethylphenyl)-isoxazole |
| 18 | 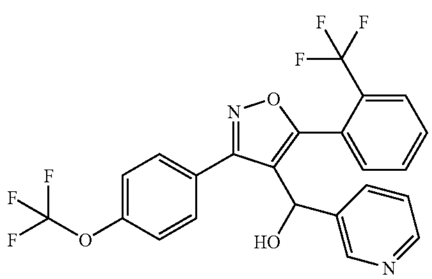 | 4-[(3-Pyridyl)hydroxymethyl]-3-(4-trifluoromethoxyphenyl)-5-(2-trifluoromethylphenyl)-isoxazole |
| 19 | 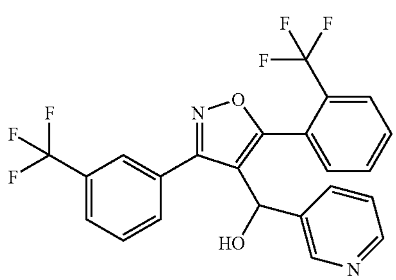 | 4-[(3-Pyridyl)hydroxymethyl]-3-(3-trifluoromethylphenyl)-5-(2-trifluoromethylphenyl)-isoxazole |
| 20 | 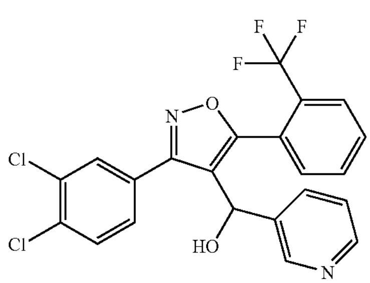 | 3-(3,4-Dichlorophenyl)-4-[(3-pyridyl)hydroxymethyl]-5-(2-trifluoromethylphenyl)-isoxazole |

-continued

| Compound No. | Structure | Chemical Name |
|---|---|---|
| 21 | 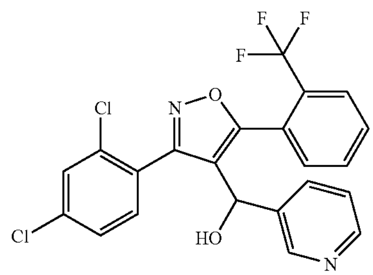 | 3-(2,4-Dichlorophenyl)-4-[(3-pyridyl)hydroxymethyl]-5-(2-trifluoromethylphenyl)-isoxazole |
| 22 | 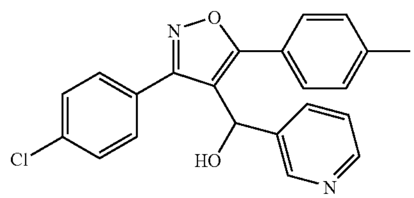 | 3-(4-Chlorophenyl)-5-(4-methylphenyl)-4-[(3-pyridyl)hydroxymethyl]-isoxazole |
| 23 | 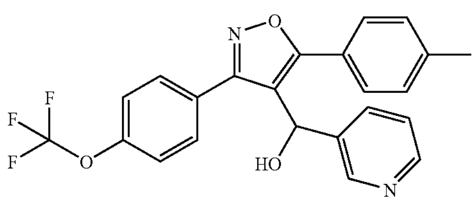 | 5-(4-Methylphenyl)-4-[(3-pyridyl)hydroxymethyl]-3-(4-trifluoromethoxyphenyl)-isoxazole |
| 24 | 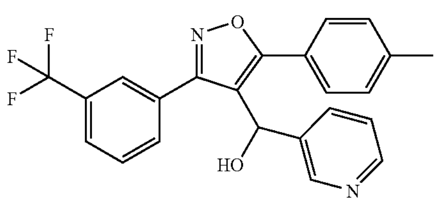 | 5-(4-Methylphenyl)-4-[(3-pyridyl)hydroxymethyl]-3-(3-trifluoromethylphenyl)-isoxazole |
| 25 | 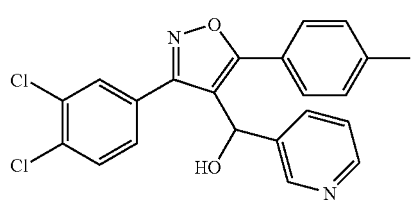 | 3-(3,4-Dichlorophenyl)-5-(4-methylphenyl)-4-[(3-pyridyl)hydroxymethyl]-isoxazole |
| 26 | 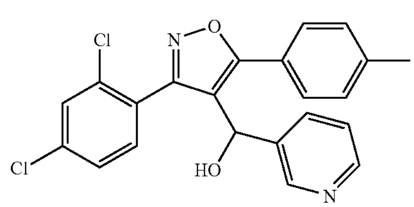 | 3-(24-Dichlorophenyl)-5-(4-methylphenyl)-4-[(3-pyridyl)hydroxymethyl]-isoxazole |
| 27 | 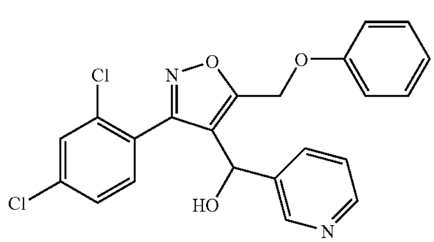 | 3-(2,4-Dichlorophenyl)-5-phenoxymethyl-4-[(3-pyridyl)hydroxymethyl]-isoxazole |

| Compound No. | Structure | Chemical Name |
|---|---|---|
| 28 | 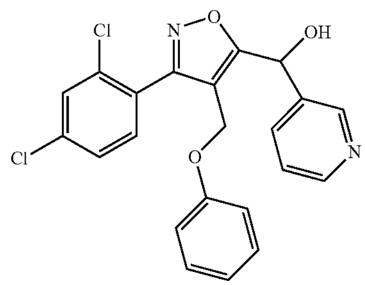 | 3-(2,4-Dichlorophenyl)-4-phenoxymethyl-5-[(3-pyridyl)hydroxymethyl]-isoxazole |
| 29 | 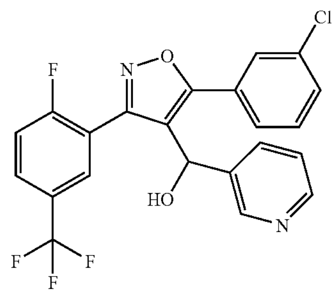 | 5-(3-Chlorophenyl)-3-(2-fluoro-5-trifluoromethylphenyl)-4-[(3-pyridyl)hydroxymethyl]-isoxazole |
| 30 | 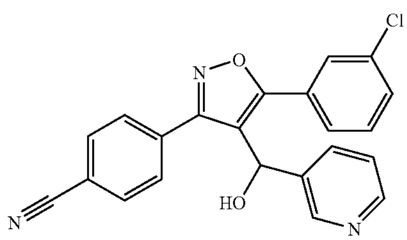 | 5-(3-Chlorophenyl)-3-(4-cyanophenyl)-4-[(3-pyridyl)hydroxymethyl]-isoxazole |
| 31 | 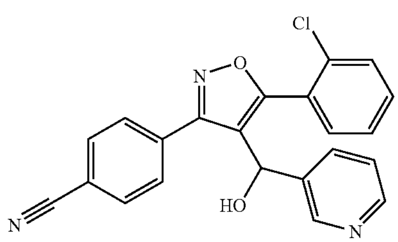 | 5-(2-Chlorophenyl)-3-(4-cyanophenyl)-4-[(3-pyridyl)hydroxymethyl]-isoxazole |
| 32 | 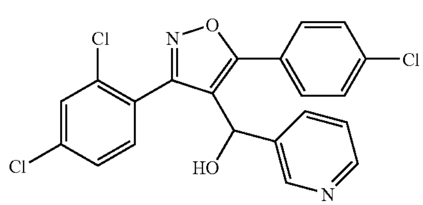 | 5-(4-Chlorophenyl)-3-(2,4-dichlorophenyl)-4-[(3-pyridyl)hydroxymethyl]-isoxazole |
| 33 | 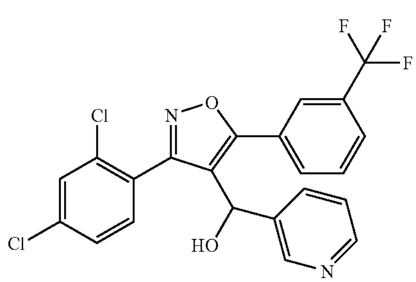 | 3-(4-Chlorophenyl)-4-[(3-pyridyl)hydroxymethyl]-5-(3-trifluoromethy)phenyl)-isoxazole |

-continued

| Compound No. | Structure | Chemical Name |
|---|---|---|
| 34 | 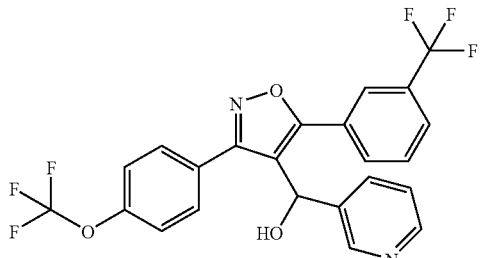 | 4-[(3-Pyridyl)hydroxymethyl]-3-(4-trifluoromethoxyphenyl)-5-(3-trifluoromethylphenyl)-isoxazole |
| 35 | 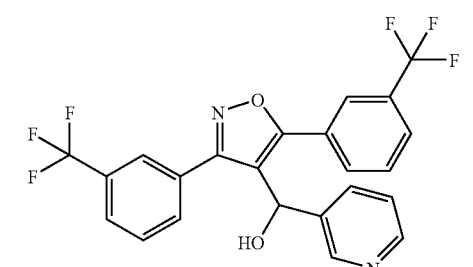 | 4-[(3-Pyridyl)hydroxymethyl]-3-(3-trifluoromethylphenyl)-5-(3-trifluoromethylphenyl)-isoxazole |
| 36 | 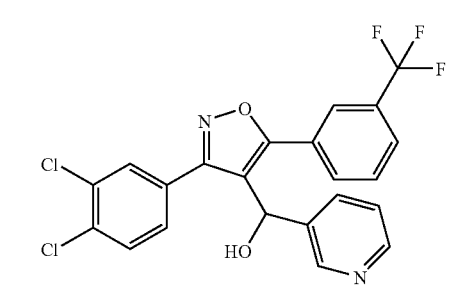 | 3-(3,4-Dichlorophenyl)-4-[(3-pyridyl)hydroxymethyl]-5-(3-trifluoromethylphenyl)-isoxazole |
| 37 | 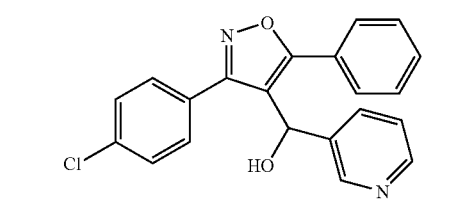 | 3-(4-Chlorophenyl)-5-phenyl-4-[(3-pyridyl)hydroxymethyl]-isoxazole |
| 38 | 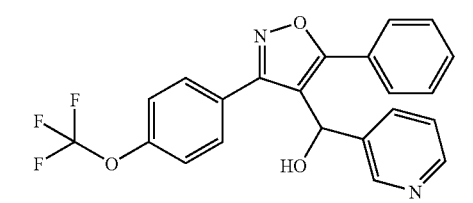 | 5-Phenyl-4-[(3-pyridyl)hydroxymethyl]-3-(4-trifluoromethoxyphenyl)-isoxazole |
| 39 | 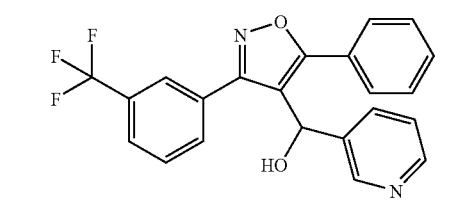 | 5-Phenyl-4-[(3-pyridyl)hydroxymethyl]-3-(4-trifluoromethylphenyl)-isoxazole |

-continued

| Compound No. | Structure | Chemical Name |
|---|---|---|
| 40 | 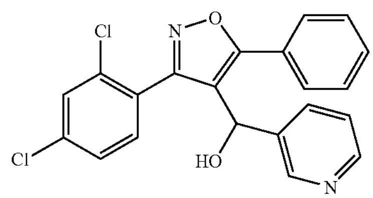 | 3-(2,4-Dichlorophenyl)-5-phenyl-4-[(3-pyridyl)hydroxymethyl]-isoxazole |
| 41 | 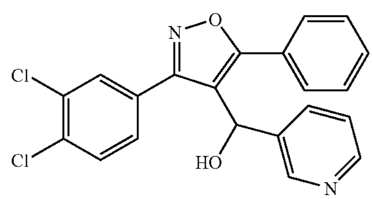 | 3-(3,4-Dichlorophenyl)-5-phenyl-4-[(3-pyridyl)hydroxymethyl]-isoxazole |
| 42 | 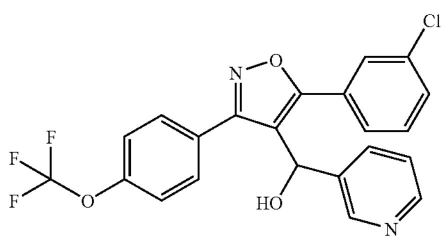 | 5-(3-Chlorophenyl)-4-[(3-pyridyl)hydroxymethyl]-3-(4-trifluoromethoxyphenyl)-isoxazole |
| 43 | 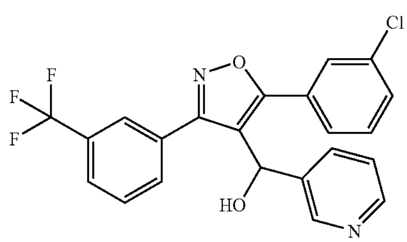 | 5-(3-Chlorophenyl)-4-[(3-pyridyl)hydroxymethyl]-3-(3-trifluoromethylphenyl)-isoxazole |
| 44 | 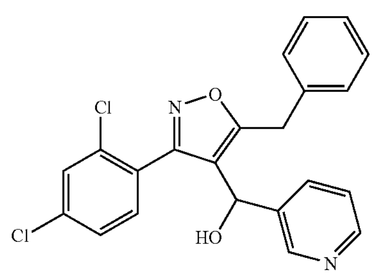 | 5-Benzyl-3-(2,4-dichlorophenyl)-4-[(3-pyridyl)hydroxymethyl]-isoxazole |
| 45 | 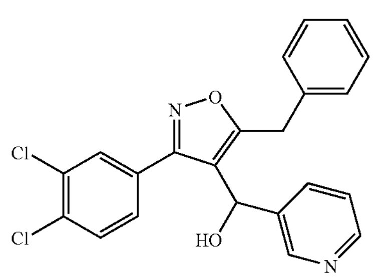 | 5-Benzyl-3-(3,4-dichlorophenyl)-4-[(3-pyridyl)hydroxymethyl]-isoxazole |

-continued

| Compound No. | Structure | Chemical Name |
|---|---|---|
| 46 | 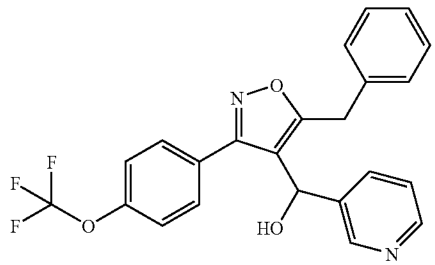 | 5-Benzyl-4-[(3-pyridyl)hydroxymethyl]-3-(4-trifluoromethoxyphenyl)-isoxazole |
| 47 | 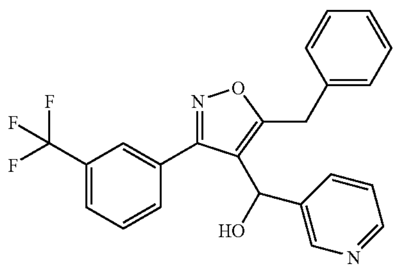 | 5-Benzyl-4-[(3-pyridyl)hydroxymethyl]-3-(3-trifluoromethylphenyl)-isoxazole |
| 48 | 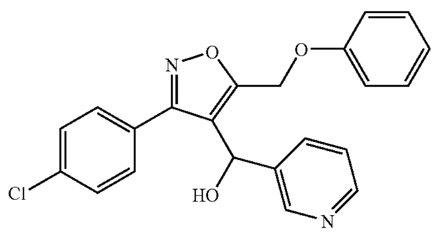 | 3-(4-Chlorophenyl)-5-phenoxymethyl-4-[(3-pyridyl)hydroxymethyl]-isoxazole |
| 49 | 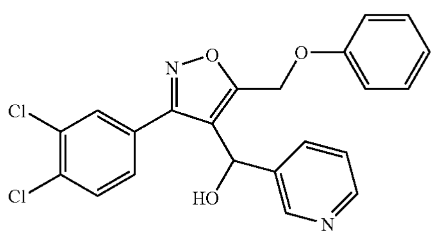 | 3-(3,4-Dichlorophenyl)-5-phenoxymethyl-4-[(3-pyridyl)hydroxymethyl]-isoxazole |
| 50 | 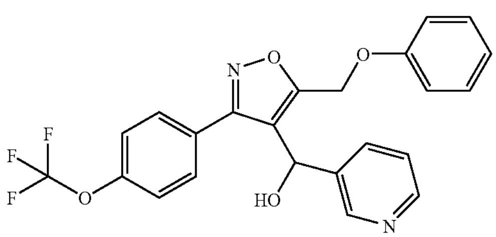 | 5-Phenoxymethyl-4-[(3-pyridyl)hydroxymethyl]-3-(4-trifluoromethoxyphenyl)-isoxazole |
| 51 | 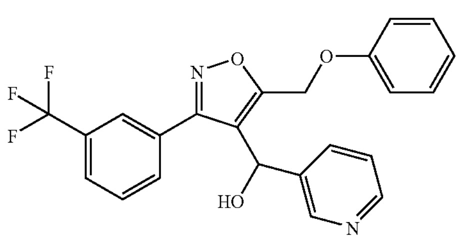 | 5-Phenoxymethyl-4-[(3-pyridyl)hydroxymethyl]-3-(3-trifluoromethylphenyl)-isoxazole |

-continued

| Compound No. | Structure | Chemical Name |
|---|---|---|
| 52 | 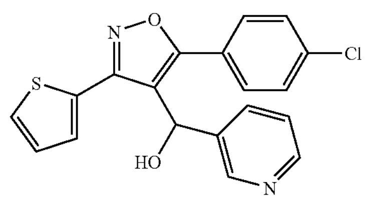 | 5-(4-Chlorophenyl)-4-[(3-pyridyl)hydroxymethyl]-3-(2-thienyl)isoxazole |
| 53 | 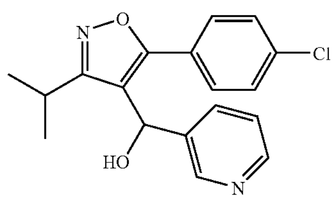 | 5-(4-Chlorophenyl)-3-isopropyl-4-[(3-pyridyl)hydroxymethyl]-isoxazole |
| 54 | 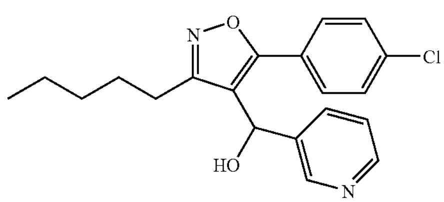 | 5-(4-Chlorophenyl)-3-pentyl-4-[(3-pyridyl)hydroxymethyl]-isoxazole |
| 55 | 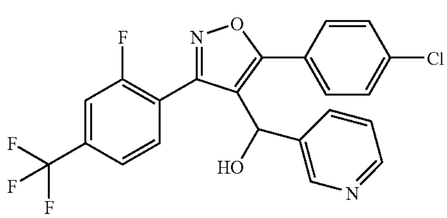 | 5-(4-Chlorophenyl)-3-(2-fluoro-4-trifluoromethylphenyl)-4-[(3-pyridyl)hydroxymethyl]-isoxazole |
| 56 | 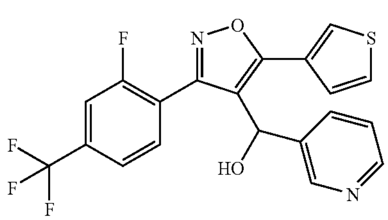 | 3-(2-Fluoro-4-trifluoromethylphenyl)-4-[(3-pyridyl)hydroxymethyl]-5-(3-thienyl)isoxazole |
| 57 | 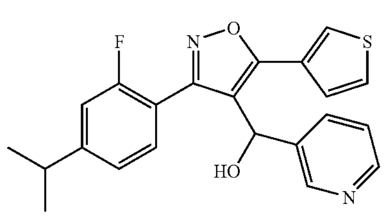 | 3-Isopropyl-4-[(3-pyridyl)hydroxymethyl]-5-(3-thienyl)isoxazole |
| 58 | 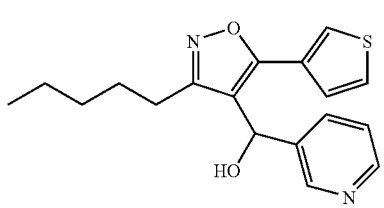 | 3-Pentyl-4-[(3-pyridyl)hydroxymethyl]-5-(3-thienyl)isoxazole |

| Compound No. | Structure | Chemical Name |
|---|---|---|
| 59 | 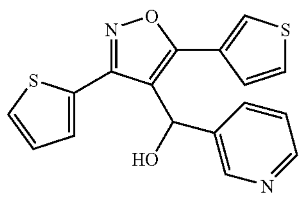 | 4-[(3-Pyridyl)hydroxymethyl]-3-(2-thienyl)-5-(3-thienyl)-isoxazole |
| 60 | 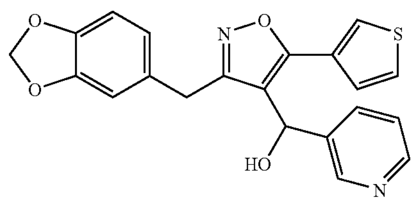 | 3-(3,4-Methylenedioxybenzyl)-4-[(3-pyridyl)hydroxymethyl]-5-(3-thienyl)isoxazole |
| 61 | 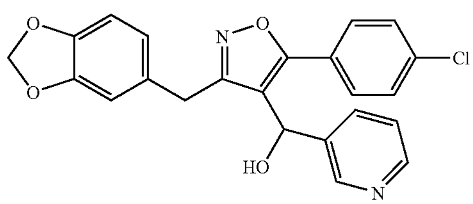 | 5-(4-Chlorophenyl)-3-(3,4-methylenedioxybenzyl)-4-[(3-pyridyl)hydroxymethyl]-isoxazole |
| 62 | 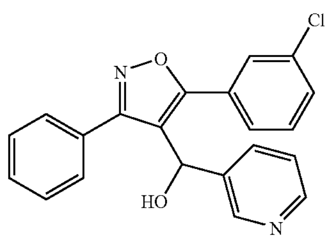 | 5-(3-Chlorophenyl)-3-phenyl-4-[(3-pyridyl)hydroxymethyl]-isoxazole |
| 63 | 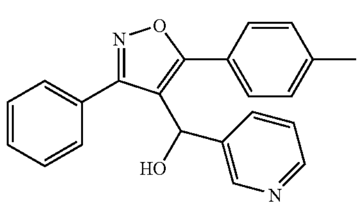 | 5-(4-Methylphenyl)-3-phenyl-4-[(3-pyridyl)hydroxymethyl]-isoxazole |
| 64 | 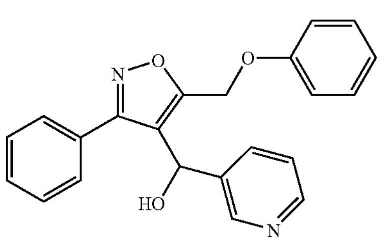 | 5-(Phenoxymethyl)-3-phenyl-4-[(3-pyridyl)hydroxymethyl]-isoxazole |
| 65 | 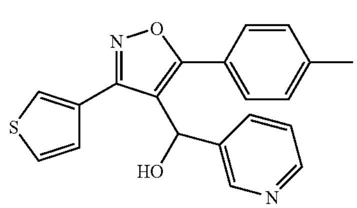 | 5-(4-Methylphenyl)-4-[(3-pyridyl)hydroxymethyl]-3-(3-thienyl)isoxazole |

| Compound No. | Structure | Chemical Name |
|---|---|---|
| 66 | 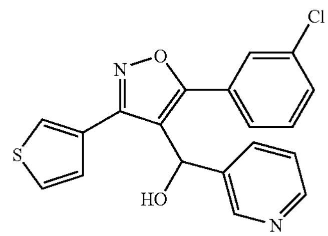 | 5-(3-Chlorophenyl)-4-[(3-pyridyl)hydroxymethyl]-3-(3-thienyl)isoxazole |
| 67 | 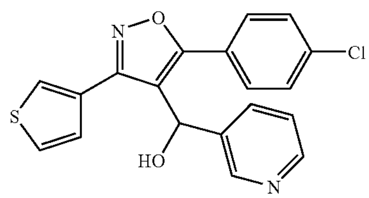 | 5-(4-Chlorophenyl)-4-[(3-pyridyl)hydroxymethyl]-3-(3-thienyl)isoxazole |
| 68 | 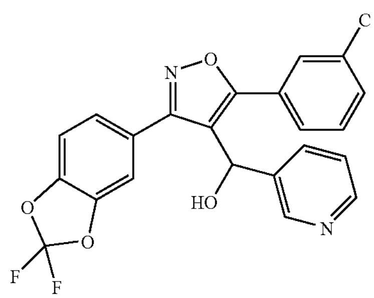 | 5-(3-Chlorophenyl)-3-(3,4-difluoromethylenedioxyphenyl)-4-[(3-pyridyl)hydroxymethyl]-isoxazole |
| 69 | 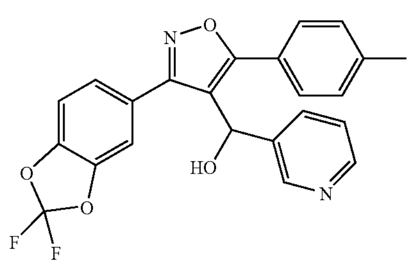 | 3-(3,4-Difluoromethylenedioxy-phenyl)-5-(4-methylphenyl)-4-[(3-pyridyl)hydroxymethyl]-isoxazole |
| 70 | 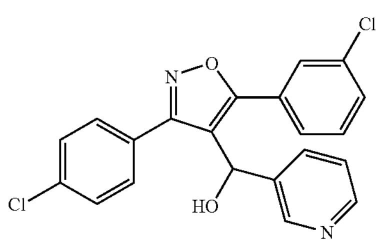 | 3-(4-Chlorophenyl)-5-(3-chlorophenyl)-4-[(3-pyridyl)hydroxymethyl]-isoxazole |
| 71 | 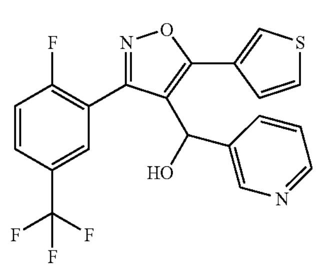 | 3-(2-Fluoro-5-trifluoromethylphenyl)-4-[(3-pyridyl)hydroxymethyl]-5-(3-thienyl)isoxazole |

| Compound No. | Structure | Chemical Name |
|---|---|---|
| 72 | 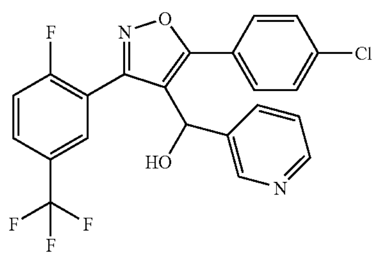 | 5-(4-Chlorophenyl)-3-(2-fluoro-5-trifluoromethylphenyl)-4-[(3-pyridyl)hydroxymethyl]-isoxazole |
| 73 | 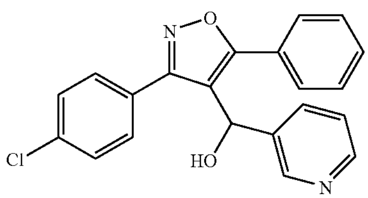 | 3-(4-Chlorophenyl)-5-phenyl-4-[(2-pyridyl)hydroxymethyl]-isoxazole |
| 74 | 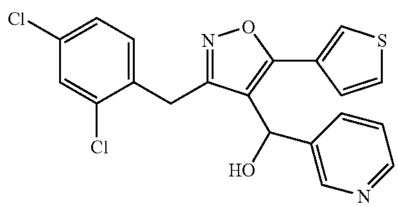 | 3-(2,4-Dichlorobenzyl)-4-[(3-pyridyl)hydroxymethyl]-5-(2-thienyl)isoxazole |
| 75 | 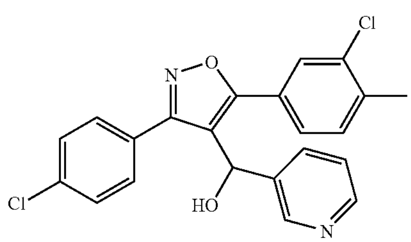 | 5-(3-Chloro-4-methylphenyl)-3-(4-chlorophenyl)-4-[(3-pyridyl)hydroxymethyl]-isoxazole |
| 76 | 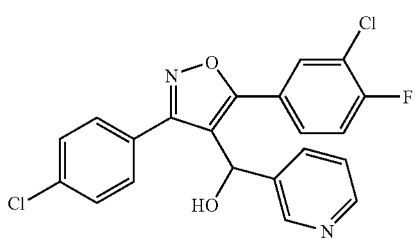 | 5-(3-Chloro-4-fluorophenyl)-3-(4-chlorophenyl)-4-[(3-pyridyl)hydroxymethyl]-isoxazole |
| 77 | 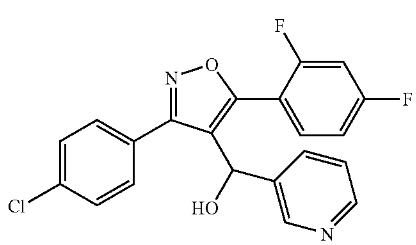 | 3-(4-Chlorophenyl)-5-(2,4-difluorophenyl)-4-[(3-pyridyl)hydroxymethyl]-isoxazole |

-continued

| Compound No. | Structure | Chemical Name |
|---|---|---|
| 78 | 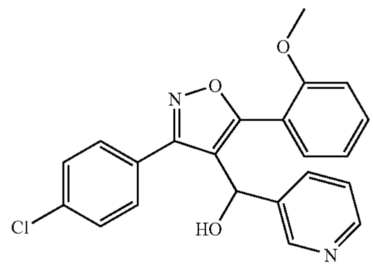 | 3-(4-Chlorophenyl)-5-(2-methoxyphenyl)-4-[(3-pyridyl)hydroxymethyl]-isoxazole |
| 79 | 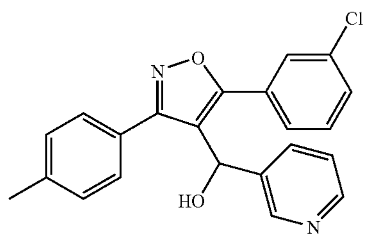 | 5-(3-Chlorophenyl)-3-(4-methylphenyl-4-[(3-pyridyl)hydroxymethyl]-isoxazole |
| 80 | 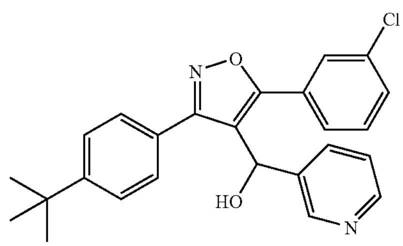 | 3-(4-tert-Butylphenyl)-5-(3-chlorophenyl)-4-[(3-pyridyl)hydroxymethyl]-isoxazole |
| 81 | 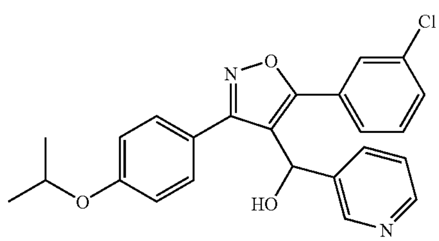 | 5-(3-Chlorophenyl)-3-(4-isopropoxyphenyl)-4-[(3-pyridyl)hydroxymethyl]-isoxazole |
| 82 | 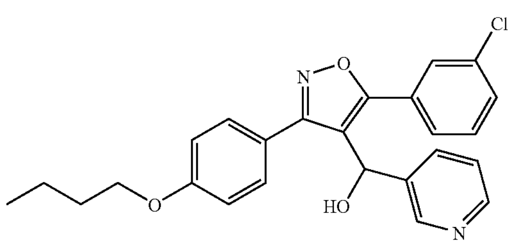 | 5-(3-Chlorophenyl)-3-(4-butoxyoxyphenyl)-4-[(3-pyridyl)hydroxymethyl]-isoxazole |
| 83 | 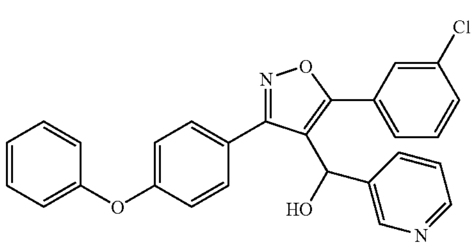 | 5-(3-Chlorophenyl)-3-(4-phenoxyphenyl)-4-[(3-pyridyl)hydroxymethyl]-isoxazole |

| Compound No. | Structure | Chemical Name |
|---|---|---|
| 84 | 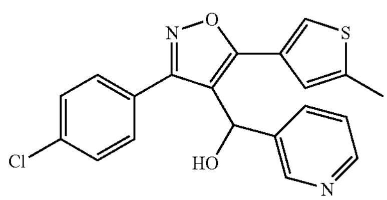 | 3-(4-Chlorophenyl)-5-(5-methyl-3-thienyl)-4-[(3-pyridyl)hydroxymethyl]-isoxazole |
| 85 | 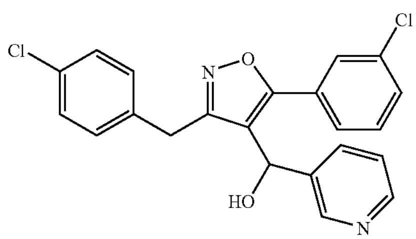 | 3-(4-Chlorobenzyl)-5(-3-chlorophenyl)-4-[(3-pyridyl)hydroxymethyl]-isoxazole |
| 86 | 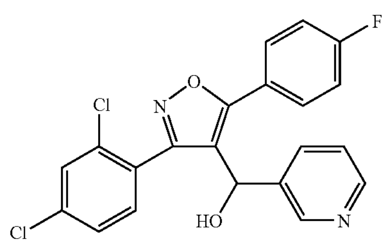 | 3-(2,4-Dichlorophenyl)-5-(4-fluorophenyl)-4-[(3-pyridyl)hydroxymethyl]-isoxazole |
| 87 | 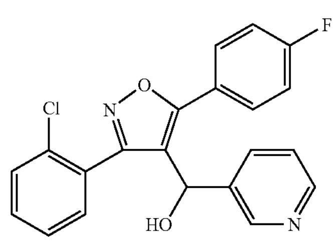 | 3-(2-Chlorophenyl)-5-(4-fluorophenyl)-4-[(3-pyridyl)hydroxymethyl]-isoxazole |
| 88 | 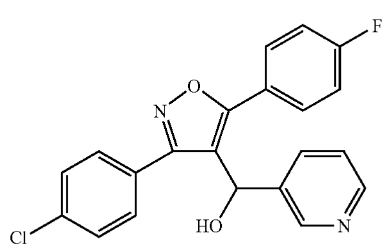 | 3-(4-Chlorophenyl)-5-(4-fluorophenyl)-4-[(3-pyridyl)hydroxymethyl]-isoxazole |
| 89 | 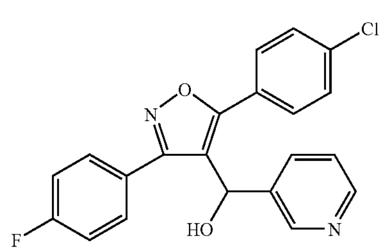 | 5-(4-Chlorophenyl)-3-(4-fluorophenyl)-4-[(3-pyridyl)hydroxymethyl]-isoxazole |

-continued

| Compound No. | Structure | Chemical Name |
|---|---|---|
| 90 | 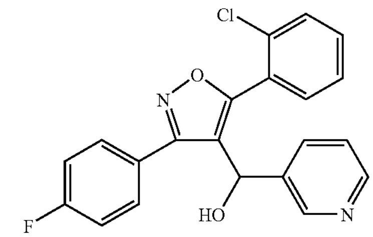 | 5-(2-Chlorophenyl)-3-(4-fluorophenyl)-4-[(3-pyridyl)hydroxymethyl]-isoxazole |
| 91 | 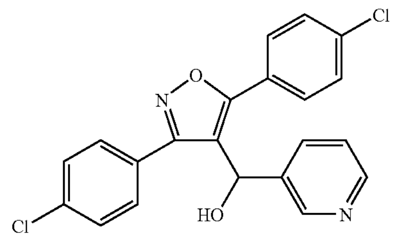 | 3-(4-Chlorophenyl)-5-(4-chlorophenyl)-4-[(3-pyridyl)hydroxymethyl]-isoxazole |
| 92 | 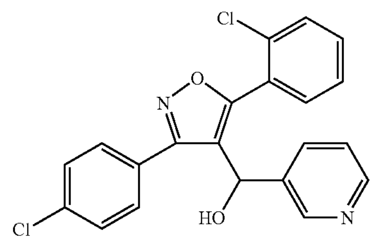 | 3-(4-Chlorophenyl)-5-(2-chlorophenyl)-4-[(3-pyridyl)hydroxymethyl]-isoxazole |
| 93 | 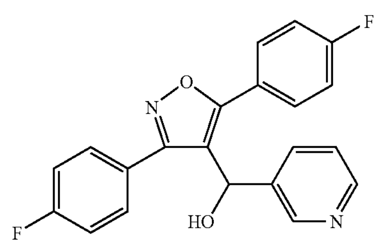 | 3-(4-Fluorophenyl)-5-(4-fluorophenyl)-4-[(3-pyridyl)hydroxymethyl]-isoxazole |
| 94 | 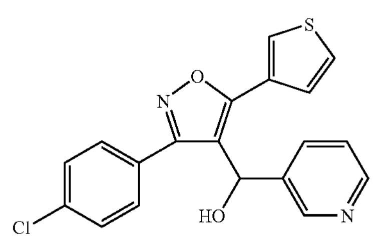 | 3-(4-Chlorophenyl)-4-[(3-pyridyl)hydroxymethyl]-5-(3-thienyl)isoxazole |
| 95 | 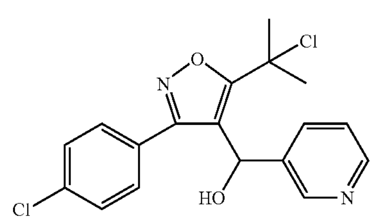 | 5-(1-Chloro-1-methylethyl)-3-(4-chlorophenyl)-4-[(3-pyridyl)hydroxymethyl]-isoxazole |

-continued

| Compound No. | Structure | Chemical Name |
|---|---|---|
| 96 | 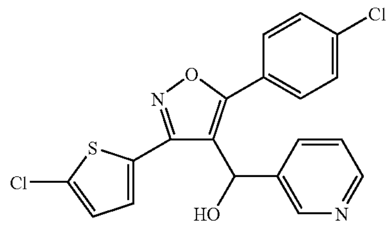 | 5-(4-Chlorophenyl)-3-(5-chloro-2-thienyl)-4-[(3-pyridyl)hydroxymethyl]-isoxazole |
| 97 | 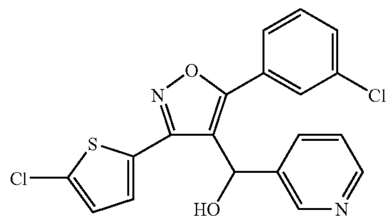 | 5-(3-Chlorophenyl)-3-(5-chloro-2-thienyl)-4-[(3-pyridyl)hydroxymethyt]-isoxazole |
| 98 | 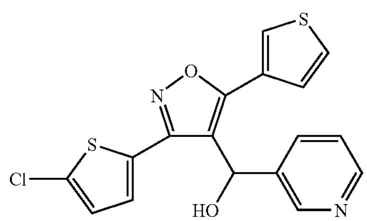 | 3-(5-Chloro-2-thienyl)-4-[(3-pyridyl)hydroxymethyl]-5-(3-thienyl)isoxazole |
| 99 | 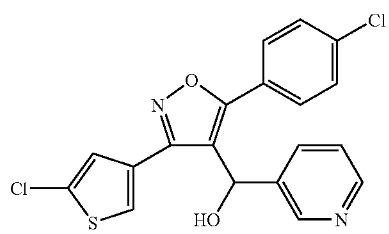 | 5-(4-Chlorophenyl)-3-(5-chloro-3-thienyl)-4-(3-pyridyl)hydroxymethyl]-isoxazole |
| 100 | 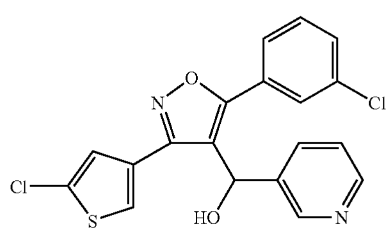 | 5-(3-Chlorophenyl)-3-(5-chloro-3-thienyl)-4-[(3-pyridyl)hydroxymethyl]-isoxazole |
| 101 | 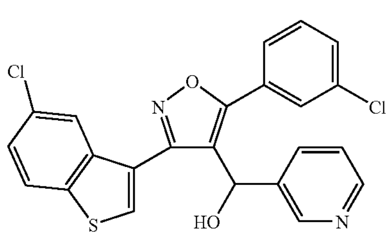 | 3-(5-Chloro-3-benzo[b]thienyl)-5-(3-chlorophenyl)-4-[(3-pyridyl)hydroxymethyl]-isoxazole |

-continued

| Compound No. | Structure | Chemical Name |
|---|---|---|
| 102 | 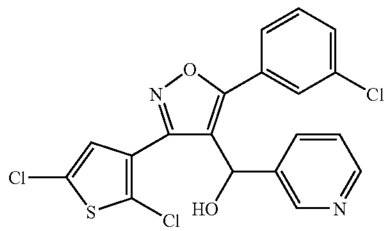 | 5-(3-Chlorophenyl)-3-(2,5-dichloro-3-thienyl)-4-[(3-pyridyl)hydroxymethyl]-isoxazole |
| 103 | 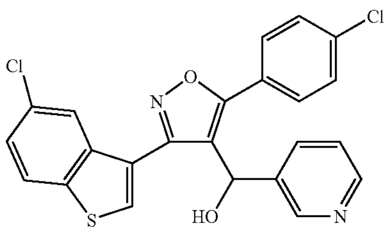 | 3-(5-Chloro-3-benzo[b]thienyl)-5-(4-chlorophenyl)-4-[(3-pyridyl)hydroxymethyl]-isoxazole |
| 104 | 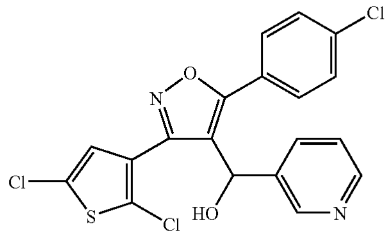 | 5-(4-Chlorophenyl)-3-(2,5-dichloro-3-thienyl)-4-[(3-pyridyl)hydroxymethyl]-isoxazole |
| 105 | 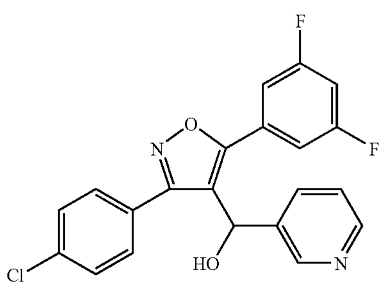 | 3-(4-Chlorophenyl)-5-(3,5-difluorophenyl)-4-[(3-pyridyl)hydroxymethyl]-isoxazole |
| 106 | 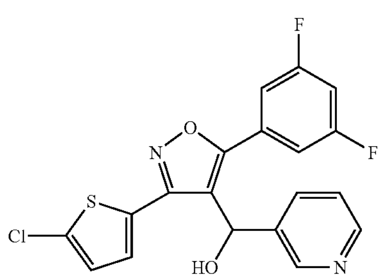 | 3-(5-Chloro-2-thienyl)-5-(3,5-difluorophenyl)-4-[(3-pyridyl)hydroxymethyl]-isoxazole |
| 107 | 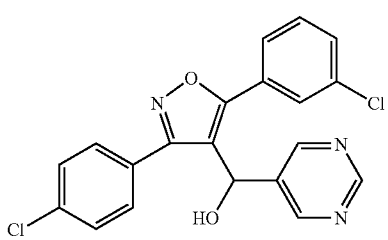 | 3-(4-Chlorophenyl)-5-(3-chlorophenyl)-4-[(5-pyrimidinyl)hydroxymethyl]-isoxazole |

-continued

| Compound No. | Structure | Chemical Name |
|---|---|---|
| 108 | 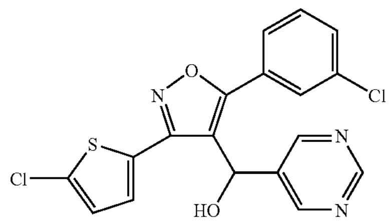 | 5-(3-Chlorophenyl)-3-(5-chloro-2-thienyl)-4-[(5-pyrimidinyl)hydroxymethyl]-isoxazole |
| 109 | 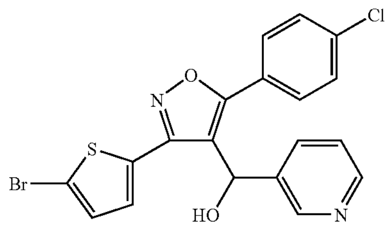 | 3-(5-Bromo-2-thienyl)-5-(4-chlorophenyl)-4-[(3-pyridyl)hydroxymethyl]-isoxazole |
| 110 | 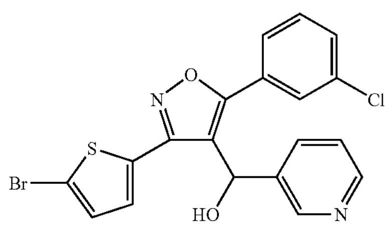 | 3-(5-Bromo-2-thienyl)-5-(3-chlorophenyl)-4-[(3-pyridyl)hydroxymethyl]-isoxazole |
| 111 | 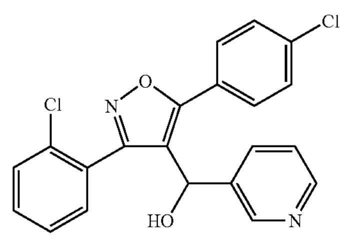 | 3-(2-Chlorophenyl)-5-(4-chlorophenyl)-4-[(3-pyridyl)hydroxymethyl]-isoxazole |
| 112 | 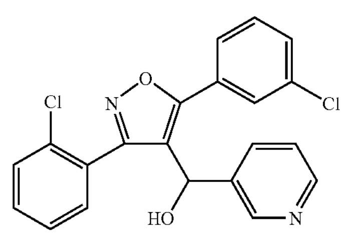 | 3-(2-Chlorophenyl)-5-(3-chlorophenyl)-4-[(3-pyridyl)hydroxymethyl]-isoxazole |
| 113 | 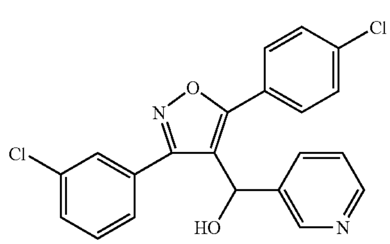 | 3-(3-Chlorophenyl)-5-(4-Chlorophenyl)-4-[(3-pyridyl)hydroxymethyl]-isoxazole |

| Compound No. | Structure | Chemical Name |
|---|---|---|
| 114 | 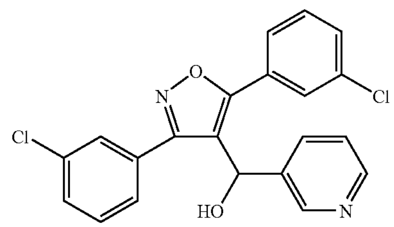 | 3-(3-Chlorophenyl)-5-(3-chlorophenyl)-4-[(3-pyridyl)hydroxymethyl]-isoxazole |
| 115 | 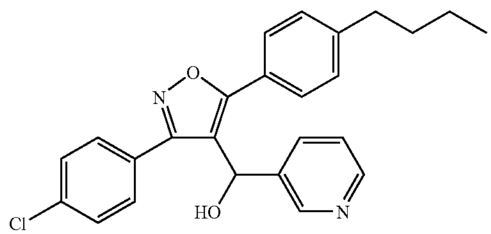 | 5-(4-Butylphenyl)-3-(4-chlorophenyl)-4-[(3-pyridyl)hydroxymethyl]-isoxazole |
| 116 | 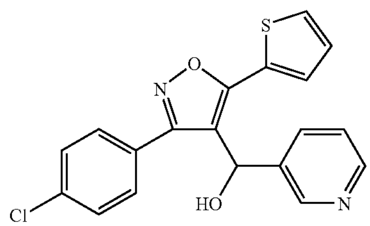 | 3-(4-Chlorophenyl)-4-[(3-pyridyl)hydroxymethyl]-5-(2-thienyl)isoxazole |
| 117 | 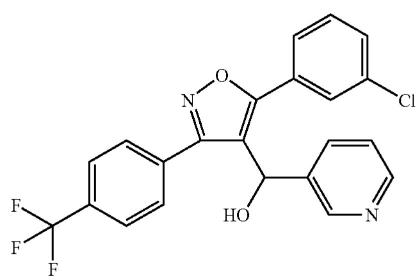 | 5-(3-Chlorophenyl)-4-[(3-pyridyl)hydroxymethyl]-3-(4-trifluorophenyl)isoxazole |
| 118 | 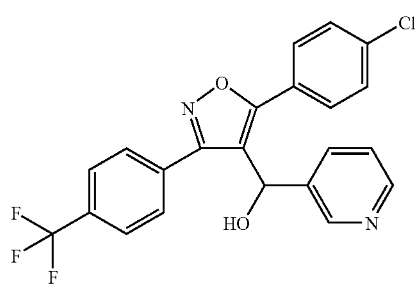 | 5-(4-Chlorophenyl)-4-[(3-pyridyl)hydroxymethyl]-3-(4-trifluorophenyl)isoxazole |
| 119 | 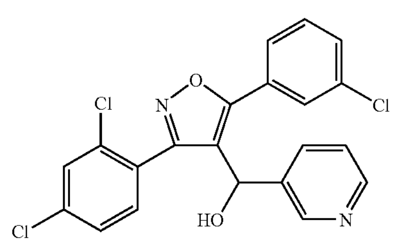 | 5-(3-Chlorophenyl)-3-(2,4-dichlorophenyl)-4-[(3-pyridyl)hydroxymethyl]-isoxazole |

-continued

| Compound No. | Structure | Chemical Name |
|---|---|---|
| 120 | 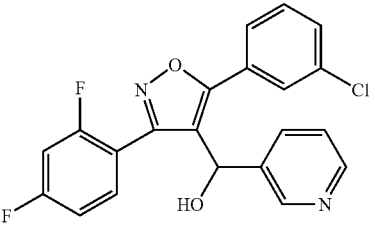 | 5-(3-Chlorophenyl)-3-(2,4-difluorophenyl)-4-[(3-pyridyl)hydroxymethyl]-isoxazole |
| 121 | 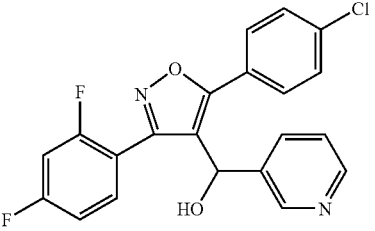 | 5-(4-Chlorophenyl)-3-(2,4-difluorophenyl)-4-[(3-pyridyl)hydroxymethyl]-isoxazole |
| 122 | 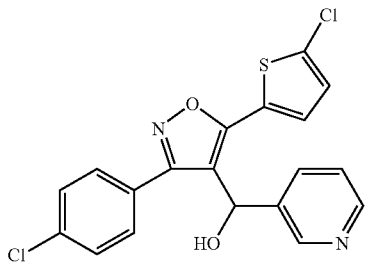 | 3-(4-Chlorophenyl)-5-(5-chloro-2-thienyl)-4-[(3-pyridyl)hydroxymethyl]-isoxazole |
| 123 | 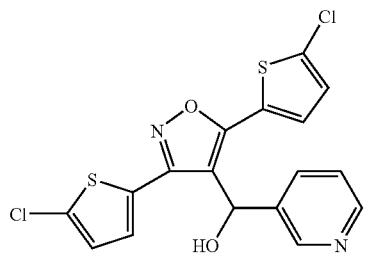 | 3-(5-Chloro-2-thienyl)-5-(5-chloro-2-thienyl)-4-[(3-pyridyl)hydroxymethyl]-isoxazole |
| 124 | 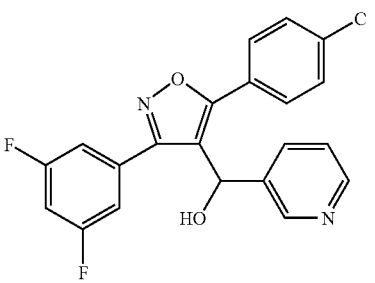 | 5-(4-Chlorophenyl)-3-(3,5-difluorophenyl)-4-[(3-pyridyl)hydroxymethyl]-isoxazole |
| 125 | 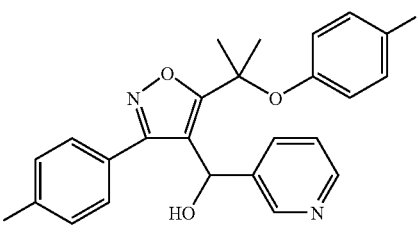 | 3-(4-Chlorophenyl)-5-[1-methyl-1-(4-chlorophenoxy)ethyl]-4-[(3-pyridyl)hydroxymethyl]-isoxazole |

-continued

| Compound No. | Structure | Chemical Name |
|---|---|---|
| 126 | 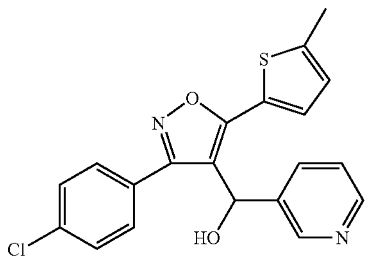 | 3-(4-Chlorophenyl)-5-(5-methyl-2-thienyl)-4-[(3-pyridyl)hydroxymethyl]-isoxazole |
| 127 | 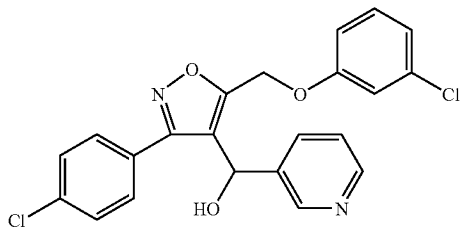 | 5-[(3-Chlorophenoxy)methyl]-3-(4-chlorophenyl)-4-[(3-pyridyl)hydroxymethyl]-isoxazole |
| 128 | 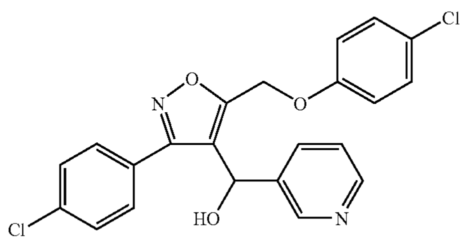 | 5-[(4-Chlorophenoxy)methyl]-3-(4-chlorophenyl)-4-[(3-pyridyl)hydroxymethyl]-isoxazole |
| 129 | 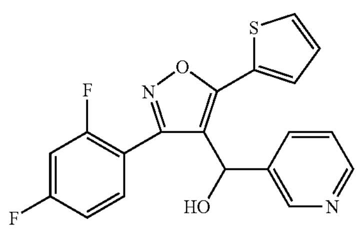 | 3-(2,4-Difluorophenyl)-4-[(3-pyridyl)hydroxymethyl]-5-(2-thienyl)isoxazole |
| 130 | 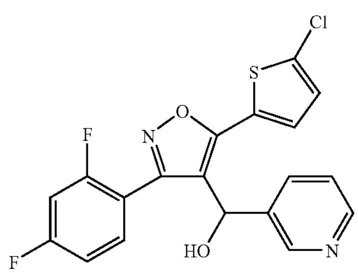 | 5-(5-Chloro-2-thienyl)-3-(2,4-difluorophenyl)-4-[(3-pyridyl)hydroxymethyl]-isoxazole |
| 131 | 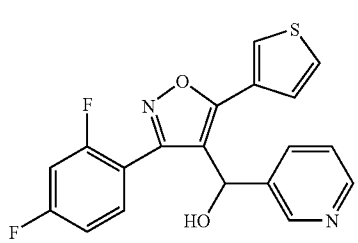 | 3-(2,4-Difluorophenyl)-4-[(3-pyridyl)hydroxymethyl]-5-(3-thienyl)isoxazole |

| Compound No. | Structure | Chemical Name |
|---|---|---|
| 132 | 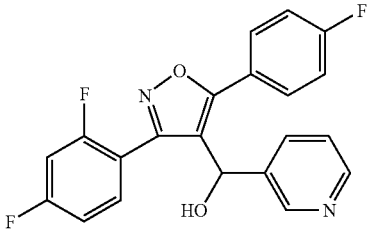 | 3-(2,4-Difluorophenyl)-5-(4-fluorophenyl)-4-[(3-pyridyl)hydroxymethyl]-isoxazole |
| 133 | 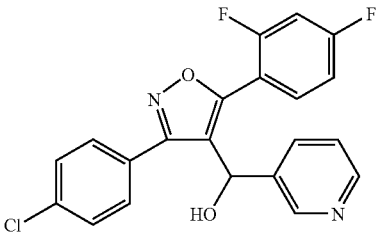 | 3-(4-Chlorophenyl)-5-(2,4-difluorophenyl)-4-[(3-pyridyl)hydroxymethyl]-isoxazole |
| 134 | 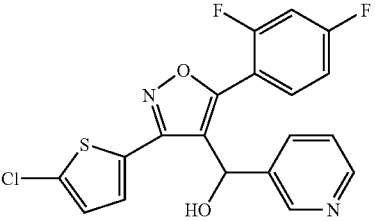 | 3-(5-Chloro-2-thienyl)-5-(2,4-difluorophenyl)-4-[(3-pyridyl)hydroxymethyl]-isoxazole |
| 135 | 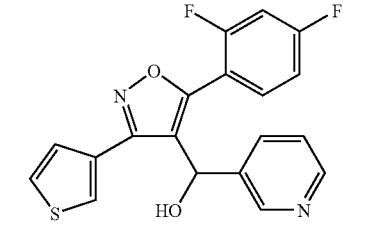 | 5-(2,4-Difluorophenyl)-4-[(3-pyridyl)hydroxymethyl]-3-(3-thienyl)isoxazole |
| 136 | 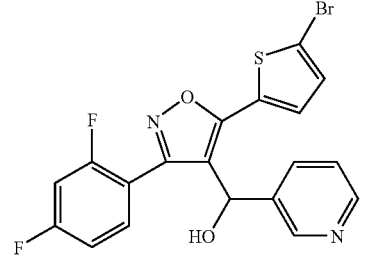 | 5-(5-Bromo-2-thienyl)-3-(2,4-difluorophenyl)-4-[(3-pyridyl)hydroxymethyl]-isoxazole |
| 137 | 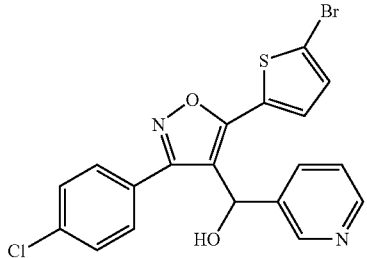 | 5-(5-Bromo-2-thienyl)-3-(4-chlorophenyl)-4-[(3-pyridyl)hydroxymethyl]-isoxazole |

-continued

| Compound No. | Structure | Chemical Name |
|---|---|---|
| 138 | 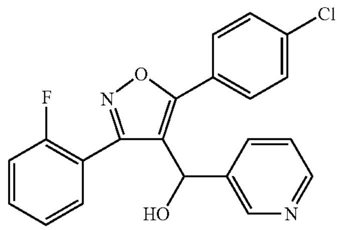 | 5-(4-Chlorophenyl)-3-(2-fluorophenyl)-4-[(3-pyridyl)hydroxymethyl]-isoxazole |
| 139 | 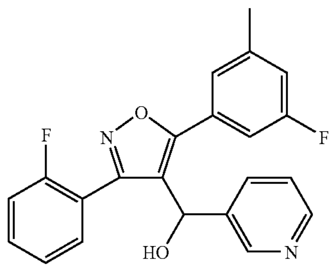 | 5-(3,5-Diflorophenyl)-3-(2-fluorophenyl)-4-[(3-pyridyl)hydroxymethyl]-isoxazole |
| 140 | 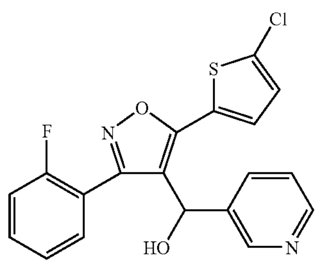 | 5-(5-Chloro-2-thienyl)-3-(2-fluorophenyl)-4-[(3-pyridyl)hydroxymethyl]-isoxazole |
| 141 | 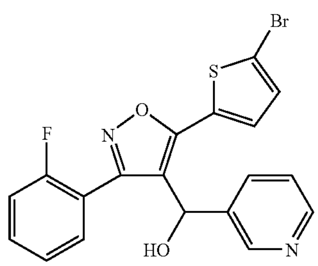 | 5-(5-Bromo-2-thienyl)-3-(2-fluorophenyl)-4-(3-pyridyl)hydroxymethyl]-isoxazole |
| 142 | 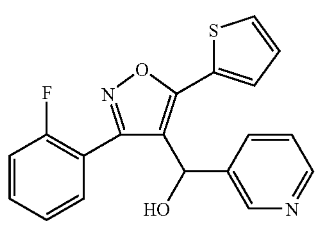 | 3-(2-Fluorophenyl)-4-[(3-pyridyl)hydroxymethyl]-5-(2-thienyl)isoxazole |
| 143 | 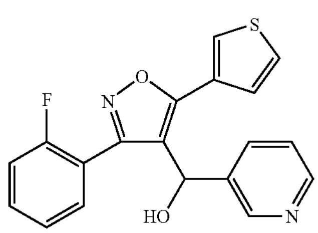 | 3-(2-Fluorophenyl)-4-[(3-pyridyl)hydroxymethyl]-5-(3-thienyl)isoxazole |

Salts. The compounds described herein and, optionally, all their isomers may be obtained in the form of their salts. Because some of the compounds I have a basic center they can, for example, form acid addition salts. Said acid addition salts are, for example, formed with mineral acids, typically sulfuric acid, a phosphoric acid or a hydrogen halide, with organic carboxylic acids, typically acetic acid, oxalic acid, malonic acid, maleic acid, fumaric acid or phthalic acid, with hydroxycarboxylic acids, typically ascorbic acid, lactic acid, malic acid, tartaric acid or citric acid, or with benzoic acid, or with organic sulfonic acids, typically methanesulfonic acid or p-toluenesulfonic acid. Together with at least one acidic group, the compounds of formula I can also form salts with bases. Suitable salts with bases are, for example, metal salts, typically alkali metal salts; or alkaline earth metal salts, e.g. sodium salts, potassium salts or magnesium salts, or salts with ammonia or an organic amine, e.g. morpholine, piperidine, pyrrolidine, a mono-, di- or trialkylamine, typically ethylamine, diethylamine, triethylamine or dimethylpropylamine, or a mono-, di- or trihydroxyalkylamine, typically mono-, di- or triethanolamine. Where appropriate, the formation of corresponding internal salts is also possible. Within the scope of this invention, agrochemical or pharmaceutically acceptable salts are preferred.

3. Agrochemical compositions and use. Active compounds of the present invention can be used to prepare agrochemical compositions and used to control fungi in like manner as other antifungal compounds. See, e.g., U.S. Pat. No. 6,617,330; see also U.S. Pat. Nos. 6,616,952; 6,569,875; 6,541,500, and 6,506,794.

Active compounds described herein can be used for protecting plants against diseases that are caused by fungi. For the purposes herein, oomycetes shall be considered fungi. The active compounds can be used in the agricultural sector and related fields as active ingredients for controlling plant pests. The active compounds can be used to inhibit or destroy the pests that occur on plants or parts of plants (fruit, blossoms, leaves, stems, tubers, roots) of different crops of useful plants, optionally while at the same time protecting also those parts of the plants that grow later e.g. from phytopathogenic micro-organisms.

Active compounds may be used as dressing agents for the treatment of plant propagation material, in particular of seeds (fruit, tubers, grains) and plant cuttings (e.g. rice), for the protection against fungal infections as well as against phytopathogenic fungi occurring in the soil.

The active compounds may be used, for example, against the phytopathogenic fungi of the following classes: Fungi imperfecti (e.g. *Botrytis, Pyricularia, Heiminthosporium, Fusarium, Septoria, Cercospora* and *Alternaria*) and Basidiomycetes (e.g. *Rhizoctonia, Hemileia, Puccinia*). Additionally, they may also be used against the Ascomycetes classes (e.g. *Venturia* and *Erysiphe, Podosphaera, Monilinia, Uncinula*) and of the Oomycetes classes (e.g. *Phytophthora, Pythium, Plasmopara*). Specific examples of fungi that may be treated include, but are not limited to, *Septoria tritici, Stagonospora nodorum, Phytophthora infestans, Botrytis cinerea, Sclerotinia homoeocarpa* and *Puccinia recondita*.

Target crops to be protected with active compounds and compositions of the invention typically comprise the following species of plants: cereal (wheat, barley, rye, oat, rice, maize, sorghum and related species); beet (sugar beet and fodder beet); pomes, drupes and soft fruit (apples, pears, plums, peaches, almonds, cherries, strawberries, raspberries and blackberries); leguminous plants (beans, lentils, peas, soybeans); oil plants (rape, mustard, poppy, olives, sunflowers, coconut, castor oil plants, cocoa beans, groundnuts); cucumber plants (pumpkins, cucumbers, melons); fiber plants (cotton, flax, hemp, jute); citrus fruit (oranges, lemons, grapefruit, mandarins); vegetables (spinach, lettuce, asparagus, cabbages, carrots, onions, tomatoes, potatoes, paprika); lauraceae (avocado, cinnamon, camphor) or plants such as tobacco, nuts, coffee, eggplants, sugar cane, tea, pepper, vines including grape-bearing vines, hops, bananas, turf and natural rubber plants, as well as ornamentals (flowers, shrubs, broad-leafed trees and evergreens, such as conifers). This list does not represent any limitation.

The active compounds can be used in the form of compositions and can be applied to the crop area or plant to be treated, simultaneously or in succession with further compounds. These further compounds can be e.g. fertilizers or micronutrient donors or other preparations which influence the growth of plants. They can also be selective herbicides as well as insecticides, fungicides, bactericides, nematicides, molluscicides, plant growth regulators, plant activators or mixtures of several of these preparations, if desired together with further carriers, surfactants or application promoting adjuvants customarily employed in the art of formulation.

The active compounds can be mixed with other fungicides, resulting in some cases in unexpected synergistic activities.

Mixing components which are particularly preferred are azoles such as azaconazole, bitertanol, propiconazole, difenoconazole, diniconazole, cyproconazole, epoxiconazole, fluquinconazole, flusilazole, flutriafol, hexaconazole, imazalil, imibenconazole, ipconazole, tebuconazole, tetraconazole, fenbuconazole, metconazole, myclobutanil, perfurazoate, penconazole, bromuconazole, pyrifenox, prochloraz, triadimefon, triadimenol, triflumizole or triticonazole; pyrimidinyl carbinoles such as ancymidol, fenarimol or nuarimol; 2-amino-pyrimidine such as bupirimate, dimethirimol or ethirimol; morpholines such as dodemorph, fenpropidin, fenpropimorph, spiroxamin or tridemorph; anilinopyrimidines such as cyprodinil, pyrimethanil or mepanipyrim; pyrroles such as fenpiclonil or fludioxonil; phenylamides such as benalaxyl, furalaxyl, metalaxyl, R-metalaxyl, ofurace or oxadixyl; benzimidazoles such as benomyl, carbendazim, debacarb, fuberidazole or thiabendazole; dicarboximides such as chlozolinate, dichlozoline, iprodine, myclozoline, procymidone or vinclozolin; carboxamides such as carboxin, fenfuram, flutolanil, mepronil, oxycarboxin or thifluzamide; guanidines such as guazatine, dodine or iminoctadine; strobilurines such as azoxystrobin, kresoxim-methyl, metominostrobin, pyraclostrobin, picoxystrobin, SSF-129, methyl 2-[(2-trifluoromethyl)-pyrid-6-yloxymethyl]-3-methoxy-acrylate or 2-[{.alpha.[(.alpha.-methyl-3-trifluoromethyl-benzyl)imino]-oxy}-o-tolyl]-glyoxylic acid-methylester-O-methyloxime (trifloxystrobin); dithiocarbamates such as ferbam, mancozeb, maneb, metiram, propineb, thiram, zineb or ziram; N-halomethylthio-dicarboximides such as captafol, captan, dichlofluanid, fluoromide, folpet or tolyfluanid; copper compounds such as Bordeaux mixture, copper hydroxide, copper oxychloride, copper sulfate, cuprous oxide, mancopper or oxine-copper; nitrophenol derivatives such as dinocap or nitrothal-isopropyl; organo phosphorous derivatives such as edifenphos, iprobenphos, isoprothiolane, phosdiphen, pyrazophos or toclofos-methyl; and other compounds of diverse structures such as acibenzolar-5-methyl, harpin, anilazine, blasticidin-S, chinomethionat, chloroneb, chlorothalonil, cymoxanil, dichlone, diclomezine, dicloran, diethofencarb, dimethomorph, dithianon, etridiazole, famoxadone, fenamidone, fentin, ferimzone, fluazinam, flusulfamide, fenhexamid, fosetyl-aluminium, hymexazol, kasugamycin, methasulfocarb, pencycuron, phthalide, polyoxins, probenazole, propamocarb, pyroquilon, quinoxyfen, quintozene, sulfur, triazoxide, tricyclazole, triforine, validamycin, (S)-5-methyl-2-methylthio-5-phenyl-3-phenylamino-3,5-di-hydroimidazol-4-one (RPA 407213), 3,5-dichloro-N-(3-chloro-1-ethyl-1-methyl-2-oxopropyl)-4-methylbenzamide (RH-7281), N-allyl-4,5-dimethyl-2-trimethylsilylthiophene-3-carboxamide (MON 65500), 4-chloro-4-cyano-N,N-dimethyl-5-p-tolylimidazole-1-sulfon-amide (IKF-916), N-(1-cyano-1,2-dimethylpropyl)-2-(2,4-dichlorophenoxy)-propionamide (AC 382042) or iprovalicarb (SZX 722).

The active compounds can be mixed with one or more systemically acquired resistance inducer ("SAR" inducer), alone or in combination with a fungicide as above. SAR inducers are known and described in, for example, U.S. Pat. No. 6,919,298. In general, a SAR inducer is any compound which has the ability to turn on resistance in a plant to a disease-causing agent, including, but not limited to a virus, a bacterium, a fungus, or combinations of these agents. In addition, an SAR inducer may induce resistance to insect feeding in a plant, as defined by Enyedi et al. (1992; *Cell* 70: 879-886). Exemplary SAR inducers cover many structural families of compounds, but are united by their ability to induce a resistance to plant diseases and/or pest feeding. One class of SAR inducers is the salicylates. The commercial SAR inducers acibenzolar-s-methyl (available as Actigard® from Syngenta), harpin protein (available as Messenger™ from Eden Biosciences), yeast extract hydrolysate from *Saccharomyces cerevisiae* (available as Keyplex® 350-DP® from Morse Enterprises Limited, Inc. of Miami, Fla.), and Oryzemate are useful in the present invention. Elicitors, including the Goemar products are another class of SAR inducers that can also be used. In addition, ethylene, its biosynthetic precursors, or ethylene releasing compounds such as Ethrel are considered SAR inducers of utility in this context. See also U.S. Pat. No. 6,919,298.

Suitable carriers and adjuvants can be solid or liquid and are substances useful in formulation technology, e.g. natural or regenerated mineral substances, solvents, dispersants, wetting agents, tackifiers, thickeners, binders or fertilizers.

A preferred method of applying an active compound of the invention, or an agrochemical composition which contains at least one of said compounds, is foliar application. The frequency of application and the rate of application will depend on the risk of infestation by the corresponding pathogen. However, the active compounds can also penetrate the plant through the roots via the soil (systemic action) by drenching the locus of the plant with a liquid formulation, or by applying the compounds in solid form to the soil, e.g. in granular form (soil application). In crops of water such as rice, such granulates can be applied to the flooded rice field. The active compounds may also be applied to seeds (coating) by impregnating the seeds or tubers either with a liquid formulation of the fungicide or coating them with a solid formulation.

The term locus as used herein is intended to embrace the fields on which the treated crop plants are growing, or where the seeds of cultivated plants are sown, or the place where the seed will be placed into the soil. The term seed is intended to embrace plant propagating material such as cuttings, seedlings, seeds, and germinated or soaked seeds.

The active compounds are used in unmodified form or, preferably, together with the adjuvants conventionally employed in the art of formulation. To this end they are conveniently formulated in known manner to emulsifiable concentrates, coatable pastes, directly sprayable or dilutable solutions, dilute emulsions, wettable powders, soluble powders, dusts, granulates, and also encapsulations e.g. in polymeric substances. As with the type of the compositions, the methods of application, such as spraying, atomizing, dusting, scattering, coating or pouring, are chosen in accordance with the intended objectives and the prevailing circumstances.

Advantageous rates of application are normally from 5 g to 2 kg of active ingredient (a.i.) per hectare (ha), preferably from 10 g to 1 kg a.i./ha, most preferably from 20 g to 600 g a.i./ha. When used as seed drenching agent, convenient dosages are from 10 mg to 1 g of active substance per kg of seeds.

The formulation, i.e. the compositions containing the compound of formula I and, if desired, a solid or liquid adjuvant, are prepared in known manner, typically by intimately mixing and/or grinding the compound with extenders, e.g. solvents, solid carriers and, optionally, surface active compounds (surfactants).

Suitable carriers and adjuvants may be solid or liquid and correspond to the substances ordinarily employed in formulation technology, such as, e.g. natural or regenerated mineral substances, solvents, dispersants, wetting agents, tackifiers, thickeners binding agents or fertilizers. Such carriers are for example described in WO 97/33890.

Further surfactants customarily employed in the art of formulation are known to the expert or can be found in the relevant literature.

The agrochemical formulations will usually contain from 0.1 to 99% by weight, preferably from 0.1 to 95% by weight, of the compound of formula I, 99.9 to 1% by weight, preferably 99.8 to 5% by weight, of a solid or liquid adjuvant, and from 0 to 25% by weight, preferably from 0.1 to 25% by weight, of a surfactant.

Whereas it is preferred to formulate commercial products as concentrates, the end user will normally use dilute formulations.

The compositions may also contain further adjuvants such as stabilizers, antifoams, viscosity regulators, binders or tackifiers as well as fertilizers, micronutrient donors or other formulations for obtaining special effects.

4. Technical materials. The compounds and combinations of the present invention may also be used in the area of controlling fungal infection (particularly by mold and mildew) of technical materials, including protecting technical material against attack of fungi and reducing or eradicating fungal infection of technical materials after such infection has occurred. Technical materials include but are not limited to organic and inorganic materials wood, paper, leather, natural and synthetic fibers, composites thereof such as particle board, plywood, wall-board and the like, woven and non-woven fabrics, construction surfaces and materials, cooling and heating system surfaces and materials, ventilation and air conditioning system surfaces and materials, and the like. The compounds and combinations according to the present invention can be applied to such materials or surfaces in an amount effective to inhibit or prevent disadvantageous effects such as decay, discoloration or mold in like manner as described above. Structures and dwellings constructed using or incorporating technical materials in which such compounds or combinations have been applied are likewise protected against attack by fungi.

5. Pharmaceutical uses. In addition to the foregoing, active compounds of the present invention can be used in the treatment of fungal infections of human and animal subjects (including but not limited to horses, cattle, sheep, dogs, cats, etc.) for medical and veterinary purposes. Examples of such infections include but are not limited to ailments such as Onychomycosis, sporotichosis, hoof rot, jungle rot, *Pseudallescheria boydii*, scopulariopsis or athletes foot, sometimes generally referred to as "white-line" disease, as well as fungal infections in immunocomprised patients such as AIDS patients and transplant patients. Thus, fungal infections may be of skin or of keratinaceous material such as hair, hooves, or nails, as well as systemic infections such as those caused by *Candida* spp., *Cryptococcus neoformans*, and *Aspergillus* spp., such as in pulmonary aspergillosis and *Pneumocystis carinii* pneumonia. Active compounds as described herein may be combined with a pharmaceutically acceptable carrier and administered or applied to such subjects or infections (e.g., topically, parenterally) in an amount effective to treat the infection in accordance with known techniques, as (for example) described in U.S. Pat. Nos. 6,680,073; 6,673,842; 6,664,292; 6,613,738; 6,423,519; 6,413,444; 6,403,063; and 6,042,845; the disclosures of which applicants specifically intend be incorporated by reference herein in their entirety.

"Pharmaceutically acceptable," is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

"Pharmaceutically-acceptable carrier" as used herein means a pharmaceutically-acceptable material, composition or vehicle, such as a liquid or solid filler, diluent, excipient, solvent or encapsulating material, involved in carrying or transporting the subject peptidomimetic agent from one organ, or portion of the body, to another organ, or portion of the body. Each carrier must be "acceptable" in the sense of being compatible with the other ingredients of the formulation and not injurious to the patient. Some examples of materials which can serve as pharmaceutically-acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Formulations of the present invention include those suitable for oral, nasal, topical (including buccal and sublingual), rectal, vaginal and/or parenteral administration. The formulations may conveniently be presented in unit dosage form and may be prepared by any methods well known in the art of pharmacy. The amount of active ingredient which can be combined with a carrier material to produce a single dosage form will vary depending upon the host being treated, the particular mode of administration. The amount of active ingredient which can be combined with a carrier material to produce a single dosage form will generally be that amount of the active ingredient which produces a therapeutic effect. Generally, out of one hundred percent, this amount will range from about 1 percent to about ninety-nine percent of active ingredient, preferably from about 5 percent to about 70 percent, most preferably from about 10 percent to about 30 percent.

Methods of preparing these formulations or compositions include the step of bringing into association a compound of the present invention with the carrier and, optionally, one or more accessory ingredients. In general, the formulations are prepared by uniformly and intimately bringing into association a peptide or peptidomimetic of the present invention with liquid carriers, or finely divided solid carriers, or both, and then, if necessary, shaping the product.

The ointments, pastes, creams and gels may contain, in addition to the active ingredient, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to a compound of this invention, excipients such as lactose, talc, silicic acid, aluminum hydroxide, calcium silicates and polyamide powder, or mixtures of these substances. Sprays can additionally contain customary propellants, such as chlorofluorohydrocarbons and volatile unsubstituted hydrocarbons, such as butane and propane.

Formulations suitable for oral administration may be presented in discrete units, such as capsules, cachets, lozenges, or tablets, each containing a predetermined amount of the active compound; as a powder or granules; as a solution or a suspension in an aqueous or non-aqueous liquid; or as an oil-in-water or water-in-oil emulsion. Such formulations may be prepared by any suitable method of pharmacy which includes the step of bringing into association the active compound and a suitable carrier (which may contain one or more accessory ingredients as noted above). In general, the formulations of the invention are prepared by uniformly and intimately admixing the active compound with a liquid or finely divided solid carrier, or both, and then, if necessary, shaping the resulting mixture. For example, a tablet may be prepared by compressing or molding a powder or granules containing the active compound, optionally with one or more accessory ingredients. Compressed tablets may be prepared by compressing, in a suitable machine, the compound in a free-flowing form, such as a powder or granules optionally mixed with a binder, lubricant, inert diluent, and/or surface active/dispersing agent(s). Molded tablets may be made by molding, in a suitable machine, the powdered compound moistened with an inert liquid binder.

Pharmaceutical compositions of this invention suitable for parenteral administration comprise one or more active compounds of the invention in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and nonaqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants. These compositions may also contain adjuvants such as preservatives, wetting agents, emulsifying agents and dispersing agents. Prevention of the action of microorganisms may be ensured by the inclusion of various antibacterial and other antifungal agents, for example, paraben, chlorobutanol, phenol sorbic acid, and the like. It may also be desirable to include isotonic agents, such as sugars, sodium chloride, and the like into the compositions. In addition, prolonged absorption of the injectable pharmaceutical form may be brought about by the inclusion of agents which delay absorption such as aluminum monostearate and gelatin.

When the compounds of the present invention are administered as pharmaceuticals, to humans and animals, they can be given per se or as a pharmaceutical composition containing, for example, 0.1 to 99.5% (more preferably, 0.5 to 90%) of active ingredient in combination with a pharmaceutically acceptable carrier.

The preparations of the present invention may be given by any suitable means of administration including orally, parenterally, topically, transdermally, rectally, etc. They are of course given by forms suitable for each administration route. For example, they are administered in tablets or capsule form, by injection, inhalation, eye lotion, ointment, suppository, etc. administration by injection, infusion or inhalation; topical by lotion or ointment; and rectal by suppositories. Topical or parenteral administration is preferred.

"Parenteral administration" and "administered parenterally" as used herein means modes of administration other than enteral and topical administration, usually by injection, and includes, without limitation, intravenous, intramuscular, intraarterial, intrathecal, intracapsular, intraorbital, intracardiac, intradermal, intraperitoneal, transtracheal, subcutaneous, subcuticular, intraarticulare, subcapsular, subarachnoid, intraspinal and intrasternal injection and infusion.

Actual dosage levels of the active ingredients in the pharmaceutical compositions of this invention may be varied so as to obtain an amount of the active ingredient which is effective to achieve the desired therapeutic response, e.g., antimycotic activity, for a particular patient, composition, and mode of administration, without being toxic to the patient. The selected dosage level will depend upon a variety of factors including the activity of the particular active compound employed, the route of administration, the time of administration, the rate of excretion of the particular active compound being employed, the duration of the treatment, other drugs, compounds and/or materials used in combination with the particular inhibitor employed, the age, sex, weight, condition, general health and prior medical history of the patient being treated, and like factors well known in the medical arts. A physician or veterinarian having ordinary skill in the art can readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved. As a general proposition, a dosage from about 0.01 or 0.1 to about 50, 1.00 or 200 mg/kg will have therapeutic efficacy, with all weights being calculated based upon the weight of the active compound, including the cases where a salt is employed.

The present invention is explained in greater detail in the following non-limiting Examples.

EXAMPLE 1

3-(2,6-Dichlorophenyl)-4-[(3-pyridyl) hydroxymethyl]-5-trimethylsilylisoxazole (Compound 1) and 3-(2,6-dichlorophenyl)-5-[(3-pyridyl) hydroxymethyl]-4-trimethylsilylisoxazole (Compound 2)

A mixture of 55 mg (0.24 mmol) of 2,6-dichloro-N-hydroxybenzenecarboximidoyl chloride, 50 mg (0.24 mmol) of 1-(3-pyridyl)-3-trimethylsilyl-2-propyn-1-ol, and 20 mg (0.24 mmol) of sodium bicarbonate in 2 mL of isopropyl alcohol was heated at 55° C. for 24 hrs. The reaction mixture was diluted with ether. The ether layer was washed with saturated sodium chloride solution, and was dried over magnesium sulfate. The drying agent was filtered off, and the ether was removed by rotoevaporation. The crude product was purified by preparative thin layer chromatography (prep TLC), and two products were isolated. The less polar product (10 mg, 0.025 mmol) was identified as 3-(2,6-dichlorophenyl)-4-[(3-pyridyl)hydroxy-methyl]-5-trimethylsilylisoxazole. $^1$H NMR (CDCl$_3$): δ 0.45 (br s, 9), 5.82 (s, 1), and 7.40 ppm (d, 1). MS m/z: 393.0 (M+H).

The more polar product was 3-(2,6-dichlorophenyl)-5-[(3-pyridyl)hydroxymethyl]-4-trimethylsilylisoxazole. $^1$H NMR (CDCl$_3$): δ 0.20 (m, 9), 6.12 (s, 1), 7.80 (d, 1), and 7.87 ppm (d, 1). MS m/z: 393.0 (M+H).

EXAMPLE 2

5-(3-Chlorophenyl)-3-(2,4-dichlorophenyl)-4-[(3-pyridyl)hydroxymethyl]isoxazole (Compound 4)

A mixture of 53 mg (0.24 mmol) of 2,4-dichloro-N-hydroxybenzenecarboximidoyl chloride, 50 mg (0.21 mmol) of 1-(3-pyridyl)-3-(3-chlorophenyl)-2-propyn-1-ol, and 26 mg (0.31 mmol) of sodium bicarbonate in 2.5 mL of isopropyl alcohol was heated at 55° C. on a rotary table shaker equipped with a heated sand bath. After 20 hrs, an additional 20 mg of 2,4-dichloro-N-hydroxybenzenecarboximidoyl chloride and 10 mg of sodium bicarbonate was added, and the reaction mixture was stirred and heated for another 16 hrs. The mixture was then diluted with ether, and the solution was washed with saturated sodium chloride and dried over magnesium sulfate. The drying agent was filtered off, and the ether was removed by rotoevaporation. The crude product was purified by prep TLC to give 15 mg (0.035 mmol) of 5-(3-chlorophenyl)-3-(2,4-dichlorophenyl)-4-[(3-pyridyl)hydroxymethyl] isoxazole. $^1$H NMR (CDCl$_3$): δ 5.92 (br s, 1), 7.04 (d of d, 1), 7.12 (d, 1), 7.72 (m, 1), 8.86 (br s, 1), and 8.29 ppm (br s, 2). MS m/z: 430.9 (M+H).

EXAMPLE 3

5-(3-Chlorophenyl)-3-(2,4-dichlorophenyl)-4-[(3-pyridyl)acetoxymethyl]isoxazole

To a solution of 43 mg (0.10 mmol) of 5-(3-chlorophenyl)-3-(2,4-dichlorophenyl)-4-[(3-pyridyl)hydroxymethyl]isoxazole in 2 mL of pyridine was added 19 μL (0.20 mmol) of acetic anhydride. The reaction was stirred overnight at room temperature, and then the pyridine was removed under vacuum. The residue was taken up in ethyl acetate, washed with saturated sodium chloride, and the ethyl acetate fraction dried over magnesium sulfate. The drying agent was filtered off, and the ethyl acetate was removed by rotoevaporation. The crude product was purified by preparative thin layer chromatography (prep TLC) to give 35 mg (0.074 mmol) of 5-(3-chlorophenyl)-3-(2,4-dichlorophenyl)-4-[(3-pyridyl) acetoxymethyl]isoxazole.

EXAMPLE 4

3-(2,4-Dichlorophenyl)-5-(1,1-dimethylethyl)-4-[(3-pyridyl)carbonyl]isoxazole

To a solution of 200 mg (1.06 mmol) of 4,4-dimethyl-1-pyridyl-2-pentyn-1-ol in 2.5 mL of dimethyl sulfoxide (DMSO) was added 443 mg (1.58 mmol) of o-iodosobenzoic acid (IBX). The reaction mixture was stirred overnight at room temperature, and then the solid was removed by filtration. The filtrate was diluted with ether, and washed with saturated sodium chloride solution. The organic fraction was separated and dried over magnesium sulfate. The drying agent was filtered off, and the ether was removed by rotoevaporation. The ketonic product, 4,4-dimethyl-1-(3-pyridyl)-2-pentyn-1-one (182 mg) was used directly without any purification.

A mixture of 72 mg (0.32 mmol) of 2,4-dichloro-N-hydroxybenzenecarboximidoyl chloride, 60 mg (0.32 mmol) of 4,4-dimethyl-1-(3-pyridyl)-2-pentyn-1-one, and 32 mg (0.38 mmol, 1.2 equivalents) of sodium bicarbonate in 2.5 mL of isopropyl alcohol was heated at 55° C. for 16 hrs on a rotary table shaker. A second addition of 25 mg of carboximidoyl chloride and 10 mg of sodium bicarbonate was followed by another 20 hrs at 55° C. The reaction mixture was cooled, diluted with ether, and then washed with saturated sodium bicarbonate. The ether fraction was dried over magnesium sulfate. The drying agent was filtered off, and the ether was removed by rotoevaporation. The crude product was purified by prep TLC to give 92 mg of oily product, 3-(2,4-dichlorophenyl)-5-(1,1-dimethylethyl)-4-[(3-pyridyl)carbonyl]isoxazole. $^1$H NMR (CDCl$_3$): δ 1.47 (s, 9), 7.90 (m, 1), 7.60 (br s, 1) and 8.72 ppm (br s, 1). MS m/z: 375.0 (M+H).

EXAMPLE 5

3-(2,4-Dichlorophenyl)-5-(1,1-dimethylethyl)-4-[(3-pyridyl)hydroxymethyl]-isoxazole (compound 7)

To a solution of 92 mg (0.24 mmol) of 3-(2,4-dichlorophenyl)-5-(1,1-dimethylethyl)-4-[(3-pyridyl)carbonyl]isoxazole in 5 mL of ethanol at 0° C. was added 20 mg (0.53 mmol) of sodium borohydride. After 2 hr, the reaction mixture was poured into water, and the product was extracted several times with ethyl acetate. The combined ethyl acetate fractions were washed with saturated sodium chloride and dried over magnesium sulfate. The drying agent was filtered off, and the ethyl acetate was removed by rotoevaporation. The crude product was purified by prep TLC to yield 68 mg (0.18 mmol) 3-(2,4-dichlorophenyl)-5-(1,1-dimethylethyl)-4-[(3-pyridyl)hydroxy-methyl]isoxazole. $^1$H NMR (CDCl$_3$): δ 1.52 (s, 9), 6.14 (br s, 1), 6.86 (d, 1), 7.38 (m, 1), 8.27 (br s, 1) and 8.33 ppm (m, 1). MS m/z: 377.0 (M+H).

EXAMPLE 6

5-(2-Chlorophenyl)-3-(2,4-dichlorophenyl)-4-[(3-pyridyl)hydroxymethyl] isoxazole (Compound 14)

To a solution of 655 mg (4.8 mmol) of 2-chlorophenylacetylene in 10 mL of tetrahydrofuran (THF) cooled to −78° C. under a nitrogen atmosphere was added 3.0 mL (4.8 mmol) of 1.6M n-butyllithium in hexane. The solution was stirred at −78° C. for 2 hrs, and then a solution of 514 mg (4.8 mmol) of 3-pyridinecarboxaldehyde in 2.5 mL of tetrahydrofuran (THF) was added. After 3.5 hrs, the reaction mixture was poured into water. The organic product was extracted with ether several times. Combined ether extracts were washed with saturated sodium bicarbonate and dried over magnesium sulfate. The drying agent was filtered off, and the ether was removed by rotoevaporation to give the oily 3-(2-chlorophenyl)-1-(3-pyridyl)-2-propyn-1-ol.

A mixture of 52 mg (0.23 mmol) of 2,4-dichloro-N-hydroxybenzenecarboximidoyl chloride, 50 mg (0.21 mmol) of 3-(2-chlorophenyl)-1-(3-pyridyl)-2-propyn-1-ol, and 30 mg (0.36 mmol) of sodium bicarbonate in 3 mL of isopropyl alcohol was heated at 55° C. overnight with shaking. The reaction mixture was cooled, diluted with ether, and then washed with saturated sodium bicarbonate. The ether fraction was dried over magnesium sulfate. The drying agent was filtered off, and the ether was removed by rotoevaporation. The crude product was purified by prep TLC to give 15 mg (0.035 mmol) of 5-(2-chlorophenyl)-3-(2,4-dichlorophenyl)-4-[(3-pyridyl)hydroxymethyl]isoxazole. $^1$H NMR (CDCl$_3$): δ 5.80 (br s, 1). MS m/z: 431.0 (M+H).

EXAMPLE 7

5-(2-Chlorophenyl)-3-(2,4-dichlorophenyl)-4-[(3-pyridyl)hydroxymethyl]isoxazole (compound 14)

A mixture of 56 mg (0.25 mmol) of 2,4-dichloro-N-hydroxybenzenecarboximidoyl chloride, 60 mg (0.25 mmol) of 3-(2-chlorophenyl)-1-(3-pyridyl)-2-propyn-1-one, and 30 mg (0.36 mmol) of sodium bicarbonate in 2.5 mL of isopropyl alcohol was heated at 55° C. overnight with shaking. An additional 30 mg of carboximidoyl chloride and 15 mg of sodium bicarbonate was then added, and the mixture was heated for another 20 hrs. The reaction mixture was cooled, diluted with ether, and then washed with saturated sodium bicarbonate. The ether fraction was dried over magnesium sulfate. The drying agent was filtered off, and the ether was removed by rotoevaporation. The crude product was purified by prep TLC to give 90 mg (0.21 mmol) of 5-(2-chlorophenyl)-3-(2,4-dichlorophenyl)-4-[(3-pyridyl)carbonyl]isoxazole. $^1$H NMR (CDCl$_3$): δ 7.16 (m, 1), 7.60 (m, 2), 7.92 (m, 1), 8.53 (br d, 1), and 8.74 ppm (br s, 1). MS m/z: 428.9 (M+H).

To a solution of 80 mg (0.19 mmol) of 5-(2-chlorophenyl)-3-(2,4-dichlorophenyl)-4-[(3-pyridyl)carbonyl]isoxazole in 3 mL of ethanol at 0° C. was added 40 mg (1.06 mmol) of sodium borohydride. The mixture was stirred for 2 hrs and then diluted with ethyl acetate. The ethyl acetate solution was washed with saturated sodium chloride solution and dried over magnesium sulfate. The drying agent was filtered off, and the ethyl acetate was removed by rotoevaporation. The crude product was purified by prep TLC to give 65 mg (0.15 mmol) of 5-(2-chlorophenyl)-3-(2,4-dichlorophenyl)-4-[(3-pyridyl)hydroxymethyl]-isoxazole. $^1$H NMR (CDCl$_3$): δ 5.80 (br s, 1), 6.97 (m, 1), 8.23 (br s, 1), and 8.28 ppm (br s, 1). MS m/z: 431.0 (M+H).

EXAMPLE 8

5-(2-Chlorophenyl)-3-(2,4-dichlorobenzyl)-4-[(3-pyridyl)hydroxymethyl] isoxazole (Compound 15)

A solution of 59 mg (0.25 mmol) of 2,4-dichlorobenzylcarboximidoyl chloride (prepared according to G. Kumaran and G. H. Kulkarni, *J. Org. Chem.* 1997, 62, 1516), 50 mg (0.21 mmol) of 3-(2-chlorophenyl)-1-(3-pyridyl)-2-propyn-1-one, and 43 μL (0.31 mmol) of triethylamine in mL of dichloromethane was heated at 55° C. in a sealed vial overnight. The reaction mixture was cooled and diluted with ether, washed with saturated sodium chloride, and dried over magnesium sulfate. The drying agent was filtered off, and solvent was removed by rotoevaporation. The crude product was purified by prep TLC to give 50 mg (0.11 mmol) 5-(2-chlorophenyl)-3-(2,4-dichlorobenzyl)-4-[(3-pyridyl)carbonyl] isoxazole. $^1$H NMR (CDCl$_3$): δ 4.23 (s, 2), 7.48 (d, 1), 7.88 (d of d, 1), 8.66 (br d, 1) and 8.70 ppm (br s, 1). MS m/z: 442.9 (M+H).

To a solution of 50 mg (0.11 mmol) of 5-(2-chlorophenyl)-3-(2,4-dichlorobenzyl)-4-[(3-pyridyl)carbonyl]isoxazole in 15 mL of THF was added 21 mg (0.56 mmol) of sodium borohydride at room temperature. After 2 hrs, the solution was diluted with ethyl acetate, washed with saturated sodium chloride, and dried over magnesium sulfate. The drying agent was filtered off, and solvent was removed by rotoevaporation. The crude product was purified by prep TLC to give 39 mg (0.088 mmol) of 5-(2-chlorophenyl)-3-(2,4-dichlorobenzyl)-4-[(3-pyridyl)hydroxymethyl]isoxazole. $^1$H NMR (CDCl$_3$): δ 3.91 (d, 1), 4.00 (d, 1), 6.97 (br s, 1), 7.64 (d, 1), 8.42 ppm (br m, 2). MS m/z: 445.0 (M+H).

EXAMPLE 9

5-(3-Chlorophenyl)-3-(2-fluoro-5-trifluoromethylphenyl)-4-[(3-pyridyl)hydroxyl-methyl]isoxazole (Compound 29)

To a solution of 643 mg (3.10 mmol) of 2-fluoro-5-trifluoromethylbenzaldehyde oxime in 5 mL of dimethyl formamide (DMF) was added 456 mg (3.41 mmol) of N-chlorosuccinimide (see K.-C. Liu, B. R. Shelton, and R. K. Howe, *J. Org. Chem.* 1980, 45, 3916). The reaction mixture was stirred at room temperature overnight, and then diluted with ethyl acetate. The ethyl acetate solution was washed with saturated sodium chloride and dried over magnesium sulfate. The drying agent was filtered off, and solvent was removed by rotoevaporation to give 675 mg (2.79 mmol) of pure white crystalline 2-fluoro-5-trifluoromethyl-N-hydroxybenzenecarboximidoyl chloride.

A mixture of 60 mg (0.25 mmol) of 2-fluoro-5-trifluoromethyl-N-hydroxybenzenecarbox-imidoyl chloride, 50 mg (0.21 mmol) of 3-(3-chlorophenyl) 1-(3-pyridyl)-2-propyn-1-one (prepared similarly to procedures noted above from lithio 3-chlorophenylacetylide and 3-pyridinecarboxaldehyde, followed by IBX oxidation), and 26 mg (0.36 mmol) of sodium bicarbonate in 2.5 mL of isopropyl alcohol was heated at 55° C. overnight with shaking. An additional 30 mg of carboximidoyl chloride and 15 mg of sodium bicarbonate were added, and the reaction was heated for another 24 hrs. The mixture was cooled and diluted with ether. The ether fraction was washed with saturated sodium chloride and dried over magnesium sulfate. The drying agent was filtered off, and solvent was removed by rotoevaporation. The residue was purified by prepTLC to give 56 mg (0.13 mmol) of 5-(3-chlorophenyl)-3-(2-fluoro-5-trifluoromethylphenyl)-4-[(3-pyridyl)carbonyl]isoxazole. $^1$H NMR (CDCl$_3$): δ 7.10 (t, 1), 7.41 (m, 1), 7.52 (m, 1), 8.65 (br s, 1), and 8.86 ppm (br s, 1). MS m/z: 447.0 (M+H).

To a solution of 56 mg (0.13 mmol) of 5-(3-chlorophenyl)-3-(2-fluoro-5-trifluoromethyl-phenyl)-4-[(3-pyridyl)carbonyl]isoxazole in 2 mL of ethanol was added 24 mg (0.63 mmol) of sodium borohydride. After 2 hrs at room temperature, the reaction mixture was diluted with ethyl acetate. The solution was washed with saturated sodium chloride and was dried over magnesium sulfate. The drying agent was filtered off, and solvent was removed by rotoevaporation. The residue was purified by prepTLC to give 44 mg (0.098 mmol) of 5-(3-chlorophenyl)-3-(2-fluoro-5-trifluoromethylphenyl)-4-[(3-pyridyl)hydroxymethyl]isoxazole. $^1$H NMR (CDCl$_3$): δ 6.01 (s, 1), 7.01 (m, 1), 7.83 (m, 1), 8.27 (m, 1), and 8.35 ppm (br s, 1). MS m/z: 449.0 (M+H).

EXAMPLE 10

Biological Screening

Fungicidal activity for the compounds described in this invention was determined using a microtiter plate format. In primary screening, test compounds in 1 μL of dimethylsulfoxide (DMSO) are delivered to individual wells of a 96-well microtiter plate. Then 100 μL of minimal media consisting of 1.5% agar is delivered to each well and allowed to cool. Finally, inoculation is carried out by the addition of 10 μL of an aqueous suspension of fungal spores to the surface of the solid agar. The plates are covered and incubated in a controlled environment at 20° C. Fungicidal activity is determined by visual inspection and photometric analysis of fungal growth after 3-5 days, depending on the pathogen. Commercial standards (azoxystrobin, benomyl, captan, chlorothalonil, famoxadone, flusilazole, and propiconazole) are included in all assays. Test pathogens include *Septoria tritici*, *Stagonospora nodorum*, *Phytophthora infestans*, and *Botrytis cinerea*. Dose response data for compounds found to be fungicidal in primary screening are obtained by screening 3-fold serial dilutions of the test compound. Fungicidal activity, noted as IC50 values in μM concentration, for certain of the compounds covered in this invention is included in the following Table 1. The coefficient of variation (ratio of standard deviation to the mean) expressed in percentage is given in parentheses.

TABLE 1

| Compound Number | B. cinerea | P. infestans | S. nodorum | S. tritici |
|---|---|---|---|---|
| 1 | E | E | E | C (b) |
| 3 | B (b) | E | B (d) | A (b) |
| 4 | B (d) | E | A (b) | A (c) |
| 7 | B (c) | E | E | E |
| 12 | B (c) | E | B (d) | A (b) |
| 13 | B (b) | E | B (d) | A (b) |

IC50(μM): A = 0-0.1; B = 0.11-1.0; C = 1.1-10; D = 11-100; E = >100
C.V. (%): (a) = 0-5; (b) = 6-15; (c) = 16-30 (d) = >30

EXAMPLE 11

Turf Trial of Compound 4

A fungicide trial was conducted on a 15-yr-old sward of creeping bentgrass v. Penncross during the spring. The turfgrass was maintained using cultural practices similar to those used in maintenance of bentgrass golf greens in the southern United States. Treatments were arranged as plots (0.5×1.0 m) in a randomized complete block design with four replications. Compound 4 was applied as a 25% active ingredient (weight/weight) air milled wetable powder. Rates of application of Compound 4 were as follows (grams active ingredient per 1000 square feet): 2.2, 4.4, and 8.8. All other fungicides were applied according to their labels (Banner MAXX 1.3ME and Insignia 20WG). The turfgrass was inoculated with autoclaved tall fescue seed infested with *Sclerotinia homoeocarpa* (common name: dollar spot) six hours after application of the initial preventive treatments. The plots received approximately 0.24 inches of irrigation water daily at 1700 hour to ensure nightly foliar wetness for infection. The Horsfall-Barratt rating scale was used to visually estimate disease severity at approximately 7-day intervals from the initial application date. Turfgrass quality was assessed using a 0-9 scale where 0=a necrotic, thin foliar canopy and 9=a dark green, dense foliar canopy. Disease and quality values were subjected to analysis of variance and means were statistically separated using the Scott-Knott cluster analysis procedure.

Dollar spot severity was high, reaching a peak >50% disease in non-treated plots. During the study, all treatments provided significant (α≦0.05) disease suppression compared to the non-treated check. Mean disease ratings <3.0% are considered acceptable for bentgrass golf greens. Based on acceptability, Banner MAXX and Compound 4 were the only treatments that provided effective control on dollar spot during most of the trial period.

All treatments significantly ($\alpha$<0.05) improved turfgrass quality compared to the non-treated check. Quality ratings >6.0 are considered acceptable for bentgrass golf greens. Highest quality ratings were associated with plots treated with either Banner MAXX or Compound 4. No appreciable phytotoxicity was observed in any of the plots. Reductions in turfgrass quality resulted mainly from dollar spot.

EXAMPLE 12

Cereal Trial of Compound 4

A field trial of Compound 4 was conducted on soft red winter wheat cultivar Sisson. Very dry weather gave rise to a low natural incidence of leaf rust (*Puccinia recondita*: PUCCRT) late in the trial. Compound 4 was applied as a 9.5% active ingredient (weight/weight) emulsifiable concentrate of the following formula (each weight/weight): 9.5% Compound 4, 9.5% m-Pyrol, 65% Surfadone LP-100, 6% Surfadone LP-300, 5% Toximul 3463F, and 5% Toximul 3464F. Rates of Compound 4 application were as follows (grams active ingredient per hectare: g a.i./ha): 140, 280 and 421. Compound 4 showed good control of the rust incidence, statistically similar to the commercial standards used in the trial [Stratego (91 and 183 g a.i./ha), Absolute (91 and 182 g a.i./ha), Quilt (101 and 160 g a.i./ha), Tilt (126 g a.i./ha), Quadris (170 g a.i./ha), Headline (82 and 110 g a.i./ha)]. Yield enhancement was observed for the highest rate of Compound 4 comparable to a commercial standard.

The foregoing is illustrative of the present invention, and is not to be construed as limiting thereof. The invention is defined by the following claims, with equivalents of the claims to be included therein.

That which is claimed is:

1. A compound of formula I:

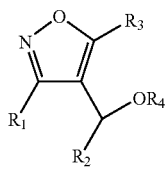

wherein:
- $R_1$ is alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkylthio, haloalkoxy, cyano, or nitro; or heteroaryl optionally substituted with halogen, alkyl, alkenyl, alkynyl, haloalkyl, alkoxy, alkylthio, haloalkoxy, cyano, or nitro;
- $R_2$ is 2-, 3- or 4-pyridyl, optionally substituted with halogen, alkyl, alkenyl, alkynyl, haloalkyl, alkoxy, alkylthio, haloalkoxy, cyano, or nitro; 5-pyrimidinyl optionally substituted with halogen, alkyl, alkenyl, alkynyl, haloalkyl, alkoxy, alkylthio, haloalkoxy, cyano, or nitro; or 2- or 5-thiazolyl optionally substituted with halogen, alkyl, alkenyl, alkynyl, alkoxy, alkylthio, haloalkyl, cyano, or nitro;
- $R_3$ is H; alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryloxyalkyl optionally substituted with halogen, alkyl, alkenyl, alkynyl, haloalkyl, alkoxy, alkylthio, haloalkoxy, cyano, or nitro; arylthioalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, or nitro; or alkylsilyl;
- $R_4$ is H; acyl; haloacyl; alkoxycarbonyl; aryloxycarbonyl; alkylaminocarbonyl; or dialkylaminocarbonyl;

or a salt of said compound.

2. The compound of claim 1 wherein $R_1$ is aryl optionally substituted with halogen, alkyl, alkenyl, alkynyl, haloalkyl, alkylthio, haloalkoxy, cyano, nitro; or heteroaryl optionally substituted with halogen, alkyl, alkenyl, alkynyl, haloalkyl, alkoxy, alkylthio, haloalkoxy, cyano, or nitro.

3. The compound of claim 1 wherein $R_1$ is 2-chlorophenyl, 4-chlorophenyl, 2,4-dichlorophenyl, 2-fluorophenyl, 2,4-difluorophenyl, 3,5-difluorophenyl, 4-trifluoro-methylphenyl, 4-trifluoromethoxyphenyl, or 2-thienyl.

4. The compound of claim 1 wherein $R_1$ is alkyl or arylalkyl optionally substituted with halogen, alkyl, alkenyl, alkynyl, haloalkyl, alkoxy, alkylthio, haloalkoxy, cyano, or nitro.

5. The compound of claim 1 wherein $R_1$ is n-pentyl, t-butyl, benzyl, or 4-chlorobenzyl.

6. The compound of claim 1 wherein $R_2$ is 2-, 3- or 4-pyridyl or 5-pyrimidinyl optionally substituted with halogen, alkyl, alkenyl, alkynyl, haloalkyl, alkoxy, alkylthio, haloalkoxy, cyano, or nitro.

7. The compound of claim 1 wherein $R_3$ is alkyl; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, nitro; or alkylsilyl.

8. The compound of claim 1 wherein $R_3$ is phenyl, 3-chlorophenyl, 4-chlorophenyl, 4-fluorophenyl, 3,5-difluorophenyl, 4-methylphenyl, 2-thienyl, 5-chloro-2-thienyl, 5-methyl-2-thienyl, 3-thienyl, t-butyl, or trimethylsilyl.

9. The compound of claim 1 wherein $R_4$ is H.

10. The compound of claim 1 wherein:
- $R_1$ is aryl optionally substituted with halogen, alkyl, alkenyl, alkynyl, haloalkyl, alkylthio, haloalkoxy, cyano, nitro; or heteroaryl optionally substituted with halogen, alkyl, alkenyl, alkynyl, haloalkyl, alkoxy, alkylthio, haloalkoxy, cyano, or nitro; and
- $R_3$ is alkyl; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, or nitro; or alkylsilyl; and
- $R_4$ is H.

11. The compound of claim 10 wherein $R_1$ is 2-chlorophenyl, 4-chlorophenyl, 2,4-dichlorophenyl, 2-fluorophenyl, 2,4-difluorophenyl, 3,5-difluorophenyl, 4-trifluoro-methylphenyl, 4-trifluoromethoxyphenyl, or 2-thienyl.

12. The compound of claim 10 wherein $R_2$ is 2-, 3- or 4-pyridyl or 5-pyrimidinyl optionally substituted with halogen, alkyl, alkenyl, alkynyl, haloalkyl, alkoxy, alkylthio, haloalkoxy, cyano, or nitro.

13. The compound of claim 10 wherein $R_3$ is phenyl, 3-chlorophenyl, 4-chlorophenyl, 4-fluorophenyl, 3,5-difluorophenyl, 4-methylphenyl, 2-thienyl, 5-chloro-2-thienyl, 5-methyl-2-thienyl, 3-thienyl, t-butyl, or trimethylsilyl.

14. The compound of claim 1 selected from the group consisting of:
3-(2,6-Dichlorophenyl)-4-[3-pyridyl)hydroxymethyl]-5-trimethylsilylisoxazole (compound 1);
3-(2,4-Dichlorophenyl)-4-[3-pyridyl)hydroxymethyl]-5-trimethylsilylisoxazole (compound 3);
5-(3-Chlorophenyl)-3-(2,4-dichlorophenyl)-4-[3-pyridyl)hydroxymethyl]isoxazole (compound 4);
3-(2,4-Dichlorophenyl)-5-(1,1-dimethylethyl)-4-[3-pyridyl)hydroxymethyl]-isoxazole (compound 7);
3-(2,4-Dichlorophenyl)-4-[3-pyridyl)hydroxymethyl]-5-(2-thienyl)isoxazole (compound 12);
3-(2,4-Dichlorophenyl)-4-[3-pyridyl)hydroxymethyl]-5-(3-thienyl)isoxazole (compound 13);
3-(4-Chlorophenyl)-5-(3-chlorophenyl)-4-[(3-pyridyl)hydroxymethyl]isoxazole (compound 70);
3-(4-Chlorophenyl)-5-(4-fluorophenyl)-4-[3-pyridyl)hydroxymethyl]isoxazole (compound 88)
3-(4-Chlorophenyl)-5-(4-chlorophenyl)-4-[(3-pyridyl)hydroxymethyl]isoxazole; (compound 91)
3-(4-Chlorophenyl)-4-[(3-pyridyl)hydroxymethyl]-5-(3-thienyl)isoxazole; (compound 94);
5-(4-Chlorophenyl)-3-(5-chloro-2-thienyl)-4-[(3-pyridyl)hydroxymethyl]-isoxazole; (compound 96);
3-(4-Chlorophenyl)-5-(3,5-difluorophenyl)-4-[(3-pyridyl)hydroxymethyl]-isoxazole; (compound 105);
3-(4-Chlorophenyl)-5-(3-chlorophenyl)-4-[(5-pyrimidinyl)hydroxymethyl]-isoxazole; (compound 107);
5-(3-Chlorophenyl)-3-(5-chloro-2-thienyl)-4-[(5-pyrimidinyl)hydroxymethyl]-isoxazole; (compound 108);
3-(5-Bromo-2-thienyl)-5-(4-chlorophenyl)-4-[3-pyridyl) hydroxymethyl]-isoxazole; (compound 109);
3-(4-Chlorophenyl)-4-[(3-pyridyl)hydroxymethyl]-5-(2-thienyl)isoxazole; (compound 116);
5-(4-Chlorophenyl)-3-(2,4-difluorophenyl)-4-[(3-pyridyl)hydroxymethyl]-isoxazole; (compound 121);
3-(4-Chlorophenyl)-5-(5-chloro-2-thienyl)-4-[(3-pyridyl)hydroxymethyl]-isoxazole; (compound 122);
3-(5-Chloro-2-thienyl)-5-(5-chloro-2-thienyl)-4-[(3-pyridyl)hydroxymethyl]-isoxazole; (compound 123);
5-(4-Chlorophenyl)-3-(3,5-difluorophenyl)-4-[(3-pyridyl)hydroxymethyl]-isoxazole; (compound 124);
and a salt thereof.

15. A composition for controlling and preventing plant pathogenic microorganisms comprising, in combination, a compound of claim 1 together with a suitable carrier.

16. The composition of claim 13, further comprising at least one additional fungicide or systemically acquired resistance inducer.

17. A method of controlling or preventing infestation of cultivated plants by pathogenic microorganisms, comprising: applying a compound according to claim 1 to said plants, parts thereof or the locus thereof in an amount effective to control said microorganisms.

18. A method according to claim 15, wherein the microorganism is a fungal organism.

19. The method of claim 16, wherein said fungal organism is selected from the group consisting of *Septoria tritici*, *Stagonospora nodorum*, *Phytophthora infestans*, *Botrytis cinerea*, *Sclerotinia homoeocarpa* and *Puccinia recondite*.

20. A method of controlling or preventing infestation of plant propagation material by pathogenic microorganisms, comprising:
applying a compound according to claim 1 to said plant propagation material in an amount effective to control said microorganisms.

21. The method of claim 18, wherein said plant propagation material comprises seeds.

22. A method according to claim 18, wherein the microorganism is a fungal organism.

23. A method of controlling or preventing infestation of a technical material by pathogenic microorganisms, comprising:
applying a compound according to claim 1 to said technical material in an amount effective to control said microorganisms.

24. A method of treating a fungal infection in a subject in need thereof, comprising:
administering a compound of claim 1 or a pharmaceutically acceptable salt thereof to said subject in an amount effective to treat said fungal infection.

25. A method of making a compound of formula I:

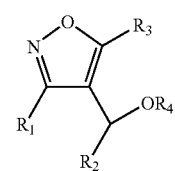

wherein:
$R_1$ is alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkylthio, haloalkoxy, cyano, or nitro; or heteroaryl optionally substituted with halogen, alkyl, alkenyl, alkynyl, haloalkyl, alkoxy, alkylthio, haloalkoxy, cyano, or nitro;

$R_2$ is 2-, 3- or 4-pyridyl, optionally substituted with halogen, alkyl, alkenyl, alkynyl, haloalkyl, alkoxy, alkylthio, haloalkoxy, cyano, or nitro; 5-pyrimidinyl optionally substituted with halogen, alkyl, alkenyl, alkynyl, haloalkyl, alkoxy, alkylthio, haloalkoxy, cyano, or nitro; or 2- or 5-thiazolyl optionally substituted with halogen, alkyl, alkenyl, alkynyl, alkoxy, alkylthio, haloalkyl, cyano, or nitro;

$R_3$ is H; alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryloxyalkyl optionally substituted with halogen, alkyl, alkenyl, alkynyl, haloalkyl, alkoxy, alkylthio, haloalkoxy, cyano, or nitro; arylthioalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, or nitro; or alkylsilyl; and $R_4$ is H;

comprising:

reacting a carboximidoyl chloride of formula II:

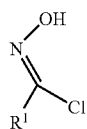

wherein $R_1$ is as given above with an acetylenic carbinol of formula III:

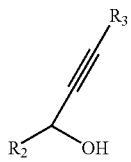

wherein $R_2$ and $R_3$ are as given above in an inert or protic solvent in the presence of a base to produce a compound of formula I.

26. The method of claim 25, wherein said solvent is an inert solvent and said base is an organic base.

27. The method of claim 25, wherein said solvent is a protic solvent and said base is an inorganic base.

28. A method of making a compound of formula I:

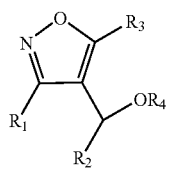

wherein:

$R_1$ is alkyl; alkoxyalkyl; haloalkyl; arylalkyl optionally substituted with halogen, alkyl, alkenyl, alkynyl, haloalkyl, alkylthio, haloalkoxy, cyano, or nitro; aryl optionally substituted with halogen, alkyl, alkenyl, alkynyl, haloalkyl, alkoxy, alkylthio, haloalkoxy, cyano, or nitro; or heteroaryl optionally substituted with halogen, alkyl, alkenyl, alkynyl, haloalkyl, alkoxy, alkylthio, haloalkoxy, cyano, or nitro;

$R_2$ is 2-, 3- or 4-pyridyl, optionally substituted with halogen, alkyl, alkenyl, alkynyl, haloalkyl, alkoxy, alkylthio, haloalkoxy, cyano, or nitro; 5-pyrimidinyl optionally substituted with halogen, alkyl, alkenyl, alkynyl, haloalkyl, alkoxy, alkylthio, haloalkoxy, cyano, or nitro; or 2- or 5-thiazolyl optionally substituted with halogen, alkyl, alkenyl, alkynyl, alkoxy, alkylthio, haloalkyl, cyano, or nitro;

$R_3$ is H; alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryloxyalkyl optionally substituted with halogen, alkyl, alkenyl, alkynyl, haloalkyl, alkoxy, alkylthio, haloalkoxy, cyano, or nitro; arylthioalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, or nitro; or alkylsilyl; and $R_4$ is H;

comprising:

reacting a carboximidoyl chloride of formula II:

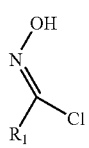

wherein $R_1$ is as given above with an acetylenic ketone of formula VI:

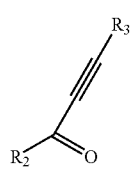

wherein $R_2$ and $R_3$ are as given above in an inert or protic solvent in the presence of a base, followed by reduction with sodium borohydride in alcoholic solvent to produce a compound of formula I.

29. The compound of claim 1 wherein $R_2$ is 5-pyrimidinyl optionally substituted with halogen, alkyl, alkenyl, alkynyl, haloalkyl, alkoxy, alkylthio, haloalkoxy, cyano, or nitro.

30. The compound of claim 1 wherein $R_2$ is 2-, 3- or 4-pyridyl optionally substituted with halogen, alkyl, alkenyl, alkynyl, haloalkyl, alkoxy, alkylthio, haloalkoxy, cyano, or nitro.

31. A compound of formula I:

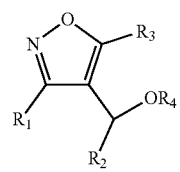

wherein:

$R_1$ is n-pentyl, t-butyl, benzyl, or 4-chlorobenzyl, 2-chlorophenyl, 4-chlorophenyl, 2,4-dichlorophenyl, 2-fluorophenyl, 2,4-difluorophenyl, 3,5-difluorophenyl, 4-trifluoro-methylphenyl, 4-trifluoromethoxyphenyl, or 2-thienyl; or heteroaryl optionally substituted with halogen, alkyl, alkenyl, alkynyl, haloalkyl, alkoxy, alkylthio, haloalkoxy, cyano, or nitro;

$R_2$ is heteroaryl, optionally substituted with halogen, alkyl, alkenyl, alkynyl, haloalkyl, alkoxy, alkylthio, haloalkoxy, cyano, or nitro; 5-pyrimidinyl optionally substituted with halogen, alkyl, alkenyl, alkynyl, haloalkyl, alkoxy, alkylthio, haloalkoxy, cyano, or nitro; or 2- or 5-thiazolyl optionally substituted with halogen, alkyl, alkenyl, alkynyl, alkoxy, alkylthio, haloalkyl, cyano, or nitro;

$R_3$ is H; alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryloxyalkyl optionally substituted with halogen, alkyl, alkenyl, alkynyl, haloalkyl, alkoxy, alkylthio, haloalkoxy, cyano, or nitro; arylthioalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, nitro; heteroaryl optionally substituted with halogen, alkyl, alkenyl, alkynyl, haloalkyl, alkoxy, alkylthio, haloalkoxy, cyano, or nitro; or alkylsilyl;

$R_4$ is H; acyl; haloacyl; alkoxycarbonyl; aryloxycarbonyl; alkylaminocarbonyl; or dialkylaminocarbonyl;

or a salt of said compound.

32. A composition for treating a fungal infection in a subject in need thereof, comprising, in combination, a compound of claim 31 or a pharmaceutically acceptable salt thereof together with a pharmaceutically acceptable carrier.

33. A compound of formula I:

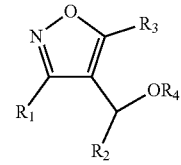

wherein:
$R_1$ is alkyl; alkoxyalkyl; haloalkyl; arylalkyl optionally substituted with halogen, alkyl, alkenyl, alkynyl, haloalkyl, alkoxy, alkylthio, haloalkoxy, cyano, or nitro; aryl optionally substituted with halogen, alkyl, alkenyl, alkynyl, haloalkyl, alkoxy, alkylthio, haloalkoxy, cyano, or nitro; or heteroaryl optionally substituted with halogen, alkyl, alkenyl, alkynyl, haloalkyl, alkoxy, alkylthio, haloalkoxy, cyano, or nitro;

$R_2$ is heteroaryl, optionally substituted with halogen, alkyl, alkenyl, alkynyl, haloalkyl, alkoxy, alkylthio, haloalkoxy, cyano, or nitro; 5-pyrimidinyl optionally substituted with halogen, alkyl, alkenyl, alkynyl, haloalkyl, alkoxy, alkylthio, haloalkoxy, cyano, or nitro; or 2- or 5-thiazolyl optionally substituted with halogen, alkyl, alkenyl, alkynyl, alkoxy, alkylthio, haloalkyl, cyano, or nitro;

$R_3$ is phenyl, 3-chlorophenyl, 4-chlorophenyl, 4-fluorophenyl, 3,5-difluorophenyl, 4-methylphenyl, 2-thienyl, 5-chloro-2-thienyl, 5-methyl-2-thienyl, 3-thienyl, t-butyl, or trimethylsilyl;

$R_4$ is H; acyl; haloacyl; alkoxycarbonyl; aryloxycarbonyl; alkylaminocarbonyl; or dialkylaminocarbonyl;

or a salt of said compound.

\* \* \* \* \*